(12) United States Patent
Kamal et al.

(10) Patent No.: US 8,519,123 B2
(45) Date of Patent: Aug. 27, 2013

(54) PYRROLO[2,1-C][1,4]BENZODIAZEPINE LINKED IMIDAZO[1,5-A]PYRIDINE CONJUGATES AS POTENTIAL ANTITUMOUR AGENTS AND PROCESS FOR THE PREPARATION THEREOF

(75) Inventors: Ahmed Kamal, Hyderabad (IN); Gadupudi Ramakrishna, Hyderabad (IN); Paidakula Raju, Hyderabad (IN); Ayinampudi Venkata Subba Rao, Hyderabad (IN); Arutla Viswanath, Hyderabad (IN); Gorre Balakishan, Hyderabad (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 13/514,270

(22) PCT Filed: Mar. 23, 2011

(86) PCT No.: PCT/IB2011/000614
§ 371 (c)(1),
(2), (4) Date: Jun. 6, 2012

(87) PCT Pub. No.: WO2012/076941
PCT Pub. Date: Jun. 14, 2012

(65) Prior Publication Data
US 2012/0253034 A1      Oct. 4, 2012

(30) Foreign Application Priority Data
Dec. 6, 2010   (IN) .......................... 2890/DEL/2011

(51) Int. Cl.
C07D 487/04      (2006.01)

(52) U.S. Cl.
USPC ........................................................ 540/496

(58) Field of Classification Search
USPC ........................................ 540/496; 544/293
See application file for complete search history.

(56) References Cited

FOREIGN PATENT DOCUMENTS
WO    WO 2004/087716 A1    10/2004

OTHER PUBLICATIONS

PCT International Search Report and Written Opinion of the International Searching Authority, PCT/IB2011/000614, Jul. 28, 2011, 10 Pages.
Kamal, A., et al., "Recent Developments in the Design, Synthesis and Structure-Activity Relationship Studies of PYRROLÄ2, 1-cÜÄ1, 4ÜBenzodiazepines as DNA-Interactive Antitumour Antibiotics," Current Medicinal Chemistry, Anti-Cancer Agents, Jan. 1, 2002, vol. 2, No. 2, pp. 215-254, Bentham Science Publishers.

*Primary Examiner* — Andrew D Kosar
*Assistant Examiner* — John S Kenyon
(74) *Attorney, Agent, or Firm* — Fenwick & West LLP

(57) ABSTRACT

The present invention provides a compound of general formula 7, useful as potential antitumour agents against five human cancer cell lines. The present invention further provides a process for the preparation of pyrrolo[2,1-c][1,4] benzodiazepine linked imidazo[1,5-a]pyridine conjugates attached through a piperazine moiety and different alkane spacers of general formula 7

GENERAL FORMULA 7

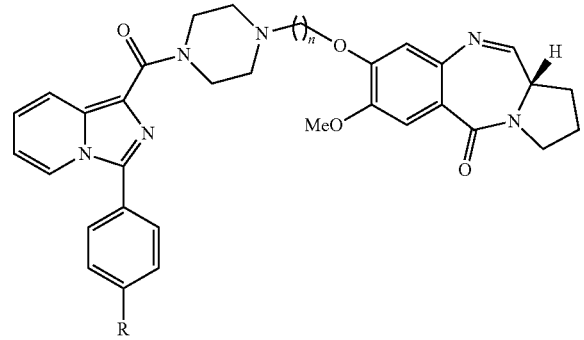

wherein R represents H, $OCH_3$, $CF_3$, CN, F or Cl;
n=3, 4, 5 or 6.

16 Claims, 1 Drawing Sheet

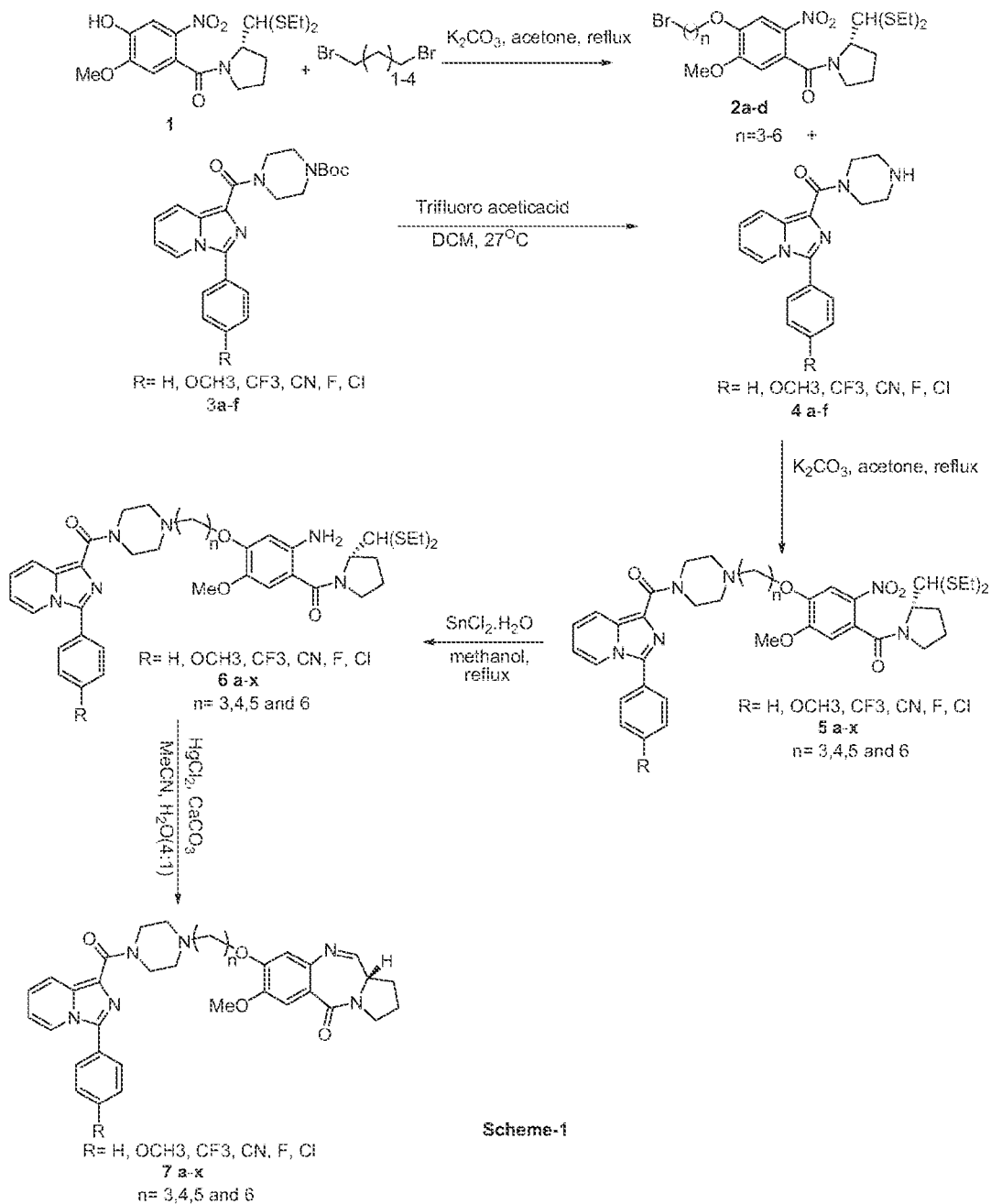
Scheme-1

PYRROLO[2,1-C][1,4]BENZODIAZEPINE LINKED IMIDAZO[1,5-A]PYRIDINE CONJUGATES AS POTENTIAL ANTITUMOUR AGENTS AND PROCESS FOR THE PREPARATION THEREOF

FIELD OF THE INVENTION

The present invention relates to pyrrolo[2,1-c][1,4]benzodiazepine linked imidazo[1,5-a]pyridine conjugates of general formula 7 as potential antitumour agents and process for the preparation thereof.

Present invention further relates to pyrrolo[2,1-c][1,4]benzodiazepine linked imidazo[1,5-a]pyridine conjugates are attached through a piperazine moiety and different alkane spacers of general formula 7

GENERAL FORMULA 7

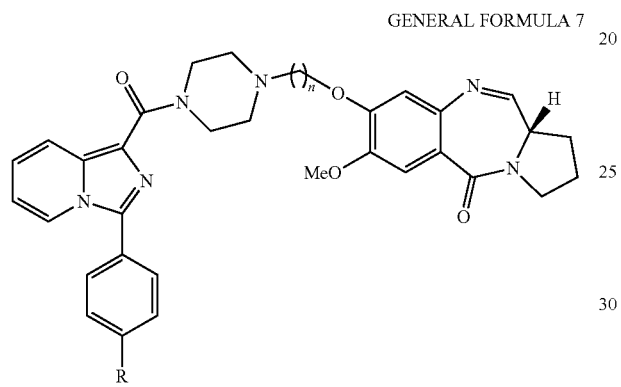

wherein R represents H, $OCH_3$, $CF_3$, CN, F or Cl; and n=3, 4, 5 or 6.

BACKGROUND OF THE INVENTION

Pyrrolo[2,1-c][1,4]benzodiazepines (PBDs), a group of potent naturally occurring antitumour antibiotics from various *Streptomyces* species, are of considerable interest because of their ability to recognize and subsequently form covalent bonds to specific base sequence of double strand DNA (Dervan, P. B. *Science* 1989, 232, 464.; Hurley, L. H. *J. Med. Chem.* 1989, 32, 2027.; Thurston, D. E.; Thompson, A. S. *Chem. Br.* 1990, 26, 767). Well-known members of this group include anthramycin, DC-81, sibiromycin, tomamycin, chicamycin and neothramycin of A and B (Hurley, L. H. *J. Antibiot.* 1977, 30, 349.; Schimizu, K.; Kawamoto, I.; Tomita, F.; Morimoto, M.; Fujimoto, K. *J. Antibiot.* 1982, 35, 992.; Lown, J. W.; Joshua, A. V. *Biochem. Pharmacol.* 1979, 28, 2017.; Thurston, D. E.; Bose, D. S. *Chem. Rev.* 1994, 94, 433.; Molina, P.; Diaz, I.; Tarraga, A. *Tetrahedron* 1995, 51, 5617.; Kamal, A.; Rao, N. V. *Chem. Commun.* 1996, 385.; Kamal, A.; Reddy, B. S. P.; Reddy, B. S. N. *Tetrahedron Lett.* 1996, 37, 6803). The cytotoxicity and antitumour activity of these agents are attributed to their property of sequence selective covalent binding to the N2 of guanine in the minor groove of duplex DNA via an acid-labile aminal bond to the electrophilic imine at the N10-C11 position (Kunimoto, S.; Masuda, T.; Kanbayashi, N.; Hamada, M.; Naganawa, H.; Miyamoto, M.; Takeuchi, T.; Unezawa, H. *J. Antibiot.*, 1980, 33, 665.; Kohn, K. W. and Speous, C. L. *J. Mol. Biol.*, 1970, 51, 551.; Hurley, L. H.; Gairpla, C. and Zmijewski, M. *Biochem. Biophys. Acta.*, 1977, 475, 521.; Kaplan, D. J. and Hurley, L. H. *Biochemistry*, 1981, 20, 7572). The molecules have a right-handed twist, which allows them to follow the curvature of the minor groove of B-form double-stranded DNA spanning three base pairs. A recent development has been the linking of two PBD units through their C-8 positions to give bisfunctional-alkylating agents capable of cross-linking DNA (Thurston, D. E.; Bose, D. S.; Thomson, A. S.; Howard, P. W.; Leoni, A.; Croker, S. J.; Jenkins, T. C.; Neidle, S. and Hurley, L. H. *J. Org. Chem.* 1996, 61, 8141).

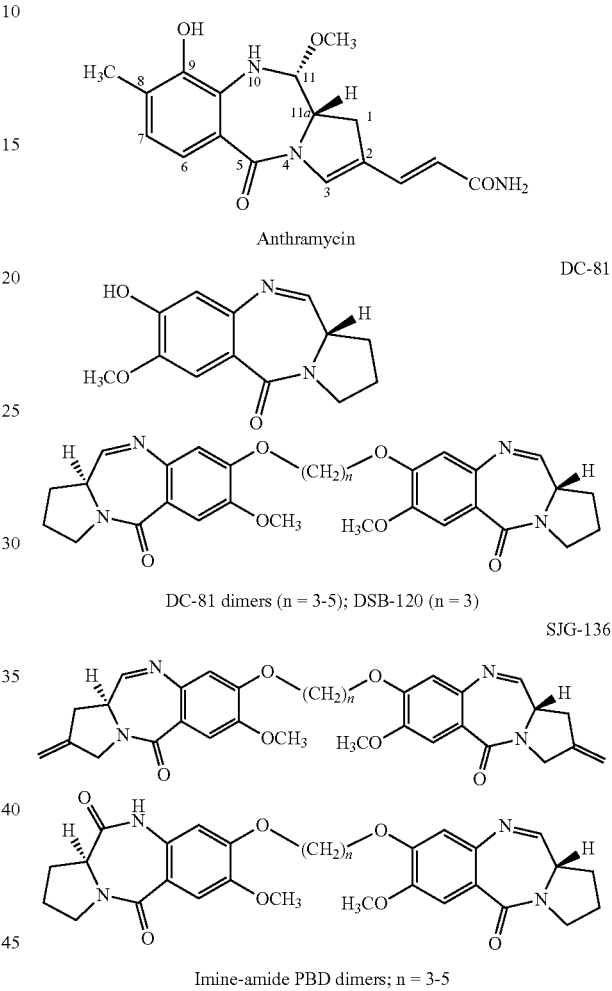

Recently, PBD dimers have been developed that comprise of two C2-exo-methylene substituted DC-81 subunits tethered through their C-8 position via an inert propanedioxy linker (Gregson, S. J.; Howard, P. W.; Hartely, J. A.; Brooks, N. A.; Adams, L. J.; Jenkins, T. C.; Kelland, L. R. and Thurston, D. E. *J. Med. Chem.* 2001, 44, 737). A non-cross-linking mixed imine-amide PBD dimers have been synthesized that have significant DNA binding ability and potent antitumour activity (Kamal, A.; Ramesh, G. Laxman, N.; Ramulu, P.; Srinivas, O.; Neelima, K.; Kondapi, A. K.; Srinu, V. B.; Nagarajaram, H. M. *J. Med. Chem.* 2002, 45, 4679).

However, the clinical efficacy for these antibiotics is hindered by several limitations, such as poor water solubility, cardiotoxicity, development of drug resistance and metabolic inactivation. Due to the excellent activity of these molecules, there is a need to develop novel derivatives which are devoid of above limitations.

Nitrogen-bridgehead merged heterocycles containing an imidazole ring have been exposed as a common structural moiety in pharmacologically important molecules, displaying a wide range of activities. Probably, the most widely worn heterocyclic system from this group is imidazo pyridine. Lately, Diaz et al. (*Eur. J. Med. Chem.* 2010, 45, 1211) reported that 6-Substituted 2-(N-trifluoroacetylamino)imidazopyridines shows cytotoxicity and induces apoptosis. Moreover, Wu et al. (*Bioorg. Med. Chem. Lett.* 2004, 14, 909) disclosed that 3,7-diarylimidazopyridines as inhibitors of the VEGF-receptor KDR. However, in the present invention the PBD and imidazopyridine moieties have been linked through piperzine moiety with alkyl side arms. These new hybrids exhibit anticancer activity and significant DNA binding affinity as illustrated in Table 1 and 2.

OBJECTIVES OF THE INVENTION

The main objective of the present invention is to provide pyrrolo[2,1-c][1,4]benzodiazepine linked imidazo[1,5-a]pyridine conjugates of general formula 7. Another objective of the present invention is to provide a process for the preparation of pyrrolo[2,1-c][1,4]benzodiazepine linked imidazo[1,5-a]pyridine conjugates of general formula 7.

Yet another objective of the present invention is to provide pyrrolo[2,1-c][1,4]benzodiazepine linked imidazo[1,5-a]pyridine conjugates of general formula 7 useful as anticancer agent.

SUMMARY OF THE INVENTION

Accordingly, present invention provides Pyrrolo[2,1-c][1,4]benzodiazepine linked imidazo[1,5-a]pyridine conjugates attached through a piperazine moiety and different alkane spacers of general formula 7

GENERAL FORMULA 7

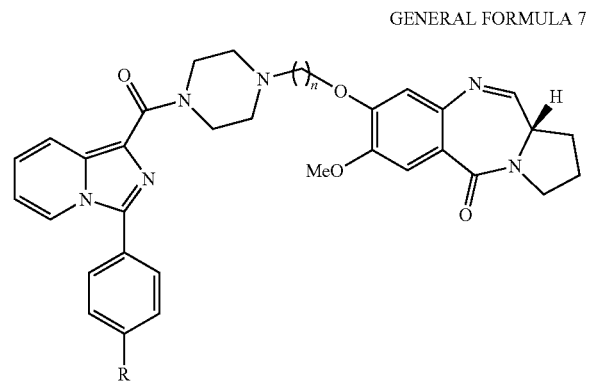

wherein R represents H, OCH$_3$, CF$_3$, CN, F or Cl; and n=3, 4, 5 or 6.

BRIEF DESCRIPTION OF THE DRAWINGS

FIG. 1: Scheme 1 represents flow diagram for the preparation of compounds of formulae 7(a-x).

DETAILED DESCRIPTION OF THE INVENTION

The present invention provides Pyrrolo[2,1-c][1,4]benzodiazepine linked imidazo[1,5-a]pyridine conjugates attached through a piperazine moiety and different alkane spacers of general formula 7

GENERAL FORMULA 7

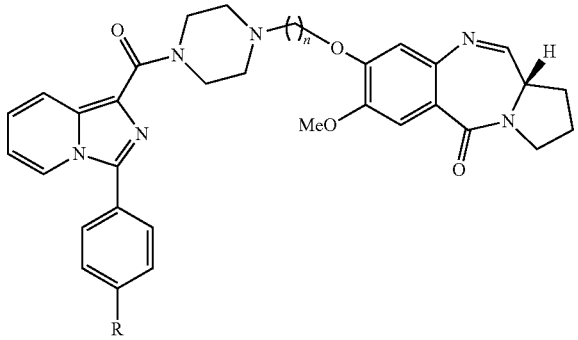

wherein R represents H, OCH$_3$, CF$_3$, CN, F or Cl; and n=3, 4, 5 or 6.

In an embodiment of the present invention, chemical formulas of the representative compounds of formula 7(a-x) are:

(11aS)-7-methoxy-8-(3-4-[(3-phenylimidazo[1,5-a]pyridin-yl)carbonyl]piperazino propoxy)-2,3,5,11a-tetrahydro-1H-benzo[e]pyrrolo[1,2-a]azepin-5-one (7a);

(11aS)-7-methoxy-8-(4-4-[(3-phenylimidazo[1,5-a]pyridin-yl)carbonyl]piperazino butoxy)-2,3,5,11a-tetrahydro-1H-benzo[e]pyrrolo[1,2-a]azepin-5-one (7b);

(11aS)-7-methoxy-8-[(5-4-[(3-phenylimidazo[1,5-a]pyridin-yl)carbonyl]piperazino pentyl)oxy]-2,3,5,11a-tetrahydro-1H-benzo[e]pyrrolo[1,2-a]azepin-5-one (7c);

(11aS)-7-methoxy-8-[(6-4-[(3-phenylimidazo[1,5-a]pyridin-1-yl)carbonyl]piperazino hexyl)oxy]-2,3,5,11a-tetrahydro-1H-benzo[e]pyrrolo[1,2-a]azepin-5-one (7d);

(11aS)-7-methoxy-8-[3-(4-[3-(4-methoxyphenyl)imidazo[1,5-a]pyridin-1-yl]carbonyl piperazino)propoxy]-2,3,5,11a-tetrahydro-1H-benzo[e]pyrrolo[1,2-a]azepin-5-one (7e);

(11aS)-7-methoxy-8-[4-(4-[3-(4-methoxyphenyl)imidazo[1,5-a]pyridin-1-yl]carbonyl piperazino)butoxy]-2,3,5,11a-tetrahydro-1H-benzo[e]pyrrolo[1,2-a]azepin-5-one (7f);

(11aS)-7-methoxy-8-[5-(4-[3-(4-methoxyphenyl)imidazo[1,5-a]pyridin-1-yl]carbonyl piperazino)pentyl]oxy-2,3,5,11a-tetrahydro-1H-benzo[e]pyrrolo[1,2-a]azepin-5-one (7g);

(11aS)-7-methoxy-8-[6-(4-[3-(4-methoxyphenyl)imidazo[1,5-a]pyridin-1-yl]carbonyl piperazino)hexyl]oxy-2,3,5,11a-tetrahydro-1H-benzo[e]pyrrolo[1,2-a]azepin-5-one (7h);

(11aS)-7-methoxy-8-3-[4-(3-[4-(trifluoromethyl)phenyl]imidazo[1,5-a]pyridin-1-yl carbonyl)piperazino]propoxy-2,3,5,11a-tetrahydro-1H-benzo[e]pyrrolo[1,2-a]azepin-5-one (7i);

(11aS)-7-methoxy-8-4-[4-(3-[4-(trifluoromethyl)phenyl]imidazo[1,5-a]pyridin-1-yl carbonyl)piperazino]butoxy-2,3,5,11a-tetrahydro-1H-benzo[e]pyrrolo[1,2-a]azepin-5-one (7j);

(11aS)-7-methoxy-8-(5-[4-(3-[4-(trifluoromethyl)phenyl]imidazo[1,5-a]pyridin-1-yl carbonyl)piperazino]pentyloxy)-2,3,5,11a-tetrahydro-1H-benzo[e]pyrrolo[1,2-a]azepin-5-one (7k);

(11aS)-7-methoxy-8-(6-[4-(3-[4-(trifluoromethyl)phenyl]imidazo[1,5-a]pyridin-1-yl carbonyl)piperazino]hexyloxy)-2,3,5,11a-tetrahydro-1H-benzo[e]pyrrolo[1,2-a]azepin-5-one (7l);

4-(1-[4-(3-[(11aS)-7-methoxy-5-oxo-2,3,5,11a-tetrahydro-1H-benzo[e]pyrrolo[1,2-a]azepin-8-yl]oxypropyl)piperazino]carbonylimidazo[1,5-a]pyridin-3-yl)benzonitrile (7m);

4-(1-[4-(4-[(11aS)-7-methoxy-5-oxo-2,3,5,11a-tetrahydro-1H-benzo[e]pyrrolo[1,2-a]azepin-8-yl]oxybutyl)piperazino]carbonylimidazo[1,5-a]pyridin-3-yl)benzonitrile (7n);

4-(1-[4-(5-[(11aS)-7-methoxy-5-oxo-2,3,5,11a-tetrahydro-1H-benzo[e]pyrrolo[1,2-a]azepin-8-yl]oxypentyl)piperazino]carbonylimidazo[1,5-a]pyridin-3-yl)benzonitrile (7o);

4-(1-[4-(6-[(11aS)-7-methoxy-5-oxo-2,3,5,11a-tetrahydro-1H-benzo[e]pyrrolo[1,2-a]azepin-8-yl]oxyhexyl)piperazino]carbonylimidazo[1,5-a]pyridin-3-yl)benzonitrile (7p);

(11aS)-8-[3-(4-[3-(4-fluorophenyl)imidazo[1,5-a]pyridin-1-yl]carbonylpiperazino)propoxy]-7-methoxy-2,3,5,11a-tetrahydro-1H-benzo[e]pyrrolo[1,2-a]azepin-5-one (7q);

(11aS)-8-[4-(4-[3-(4-fluorophenyl)imidazo[1,5-a]pyridin-1-yl]carbonylpiperazino)butoxy]-7-methoxy-2,3,5,11a-tetrahydro-1H-benzo[e]pyrrolo[1,2-a]azepin-5-one (7r);

(11aS)-8-[5-(4-[3-(4-fluorophenyl)imidazo[1,5-a]pyridin-1-yl]carbonylpiperazino)pentyl]oxy-7-methoxy-2,3,5,11a-tetrahydro-1H-benzo[e]pyrrolo[1,2-a]azepin-5-one (7s);

(11aS)-8-[6-(4-[3-(4-fluorophenyl)imidazo[1,5-a]pyridin-1-yl]carbonylpiperazino)hexyl]oxy-7-methoxy-2,3,5,11a-tetrahydro-1H-benzo[e]pyrrolo[1,2-a]azepin-5-one (7t);

(11aS)-8-[3-(4-[3-(4-chlorophenyl)imidazo[1,5-a]pyridin-1-yl]carbonylpiperazino)propoxy]-7-methoxy-2,3,5,11a-tetrahydro-1H-benzo[e]pyrrolo[1,2-a]azepin-5-one (7u);

(11aS)-8-[4-(4-[3-(4-chlorophenyl)imidazo[1,5-a]pyridin-1-yl]carbonylpiperazino)butoxy]-7-methoxy-2,3,5,11a-tetrahydro-1H-benzo[e]pyrrolo[1,2-a]azepin-5-one (7v);

(11aS)-8-[5-(4-[3-(4-chlorophenyl)imidazo[1,5-a]pyridin-1-yl]carbonylpiperazino)pentyl]oxy-7-methoxy-2,3,5,11a-tetrahydro-1H-benzo[e]pyrrolo[1,2-a]azepin-5-one (7w);

(11aS)-8-[6-(4-[3-(4-chlorophenyl)imidazo[1,5-a]pyridin-1-yl]carbonylpiperazino)hexyl]oxy-7-methoxy-2,3,5,11a-tetrahydro-1H-benzo[e]pyrrolo[1,2-a]azepin-5-one (7x);

In another embodiment of the present invention, the structural formulae of the representative compounds 7(a-x) are:

(7a)

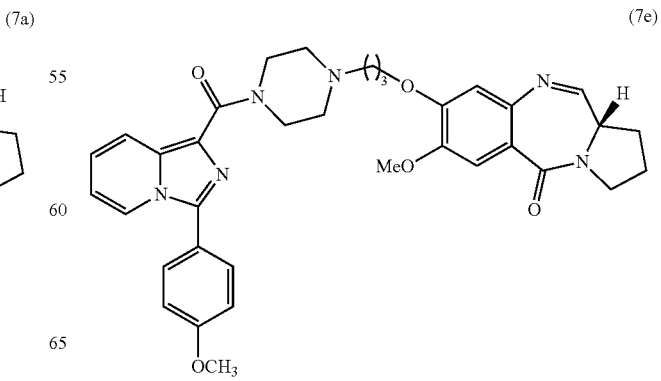

(7b)

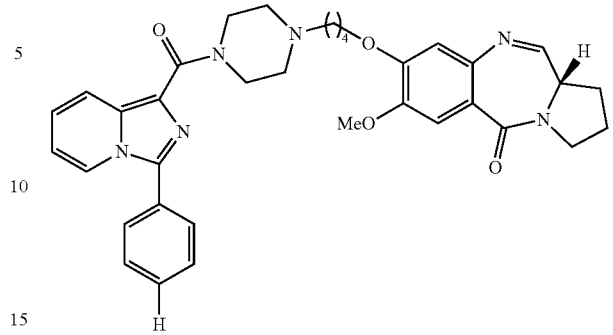

(7c)

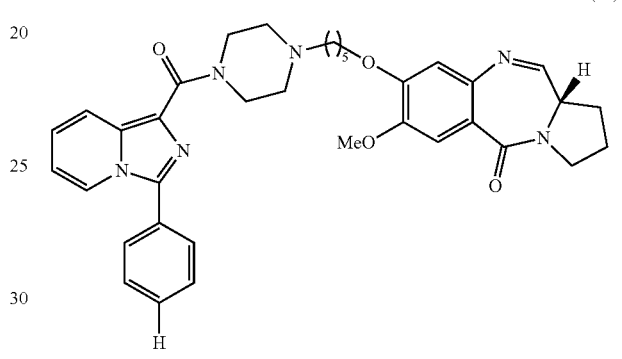

(7d)

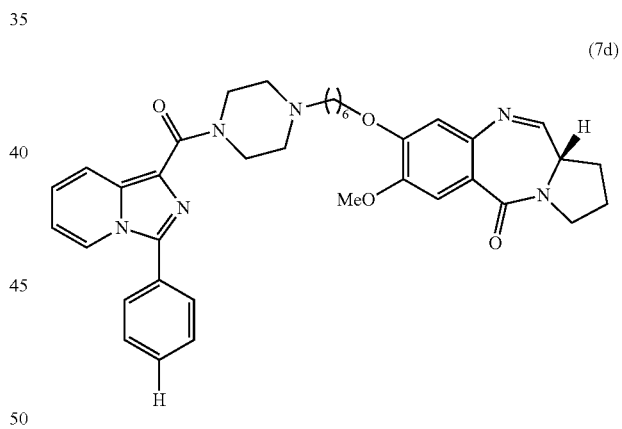

(7e)

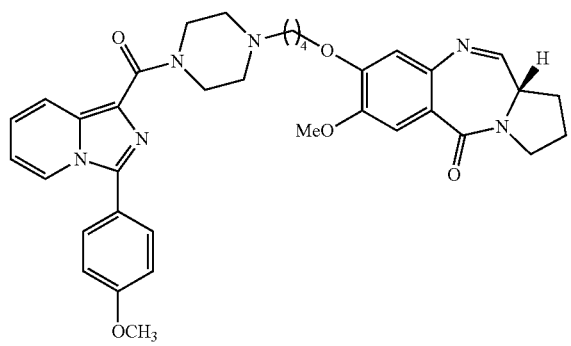
(7f)
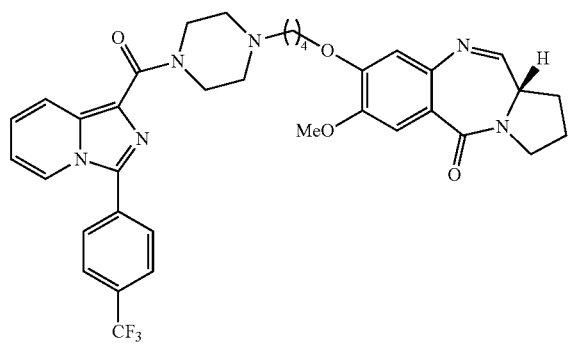
(7j)
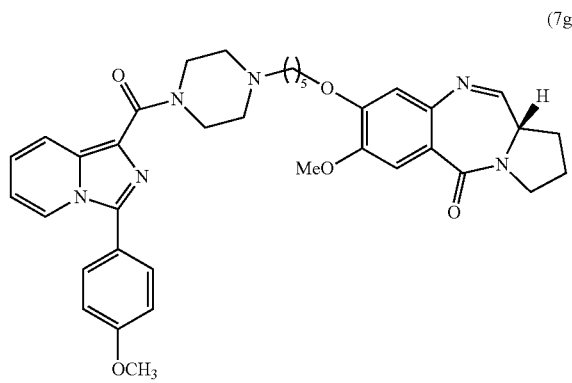
(7g)
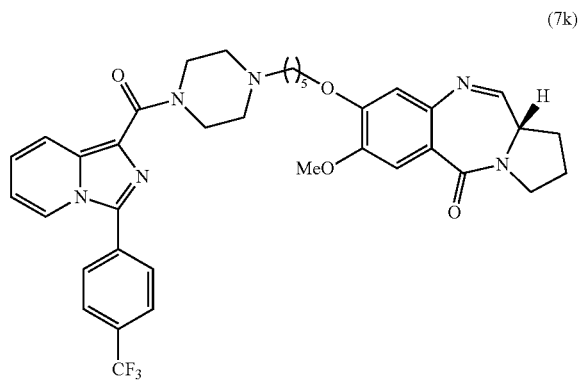
(7k)
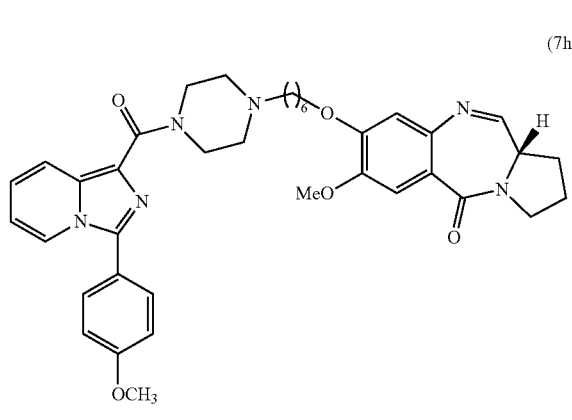
(7h)
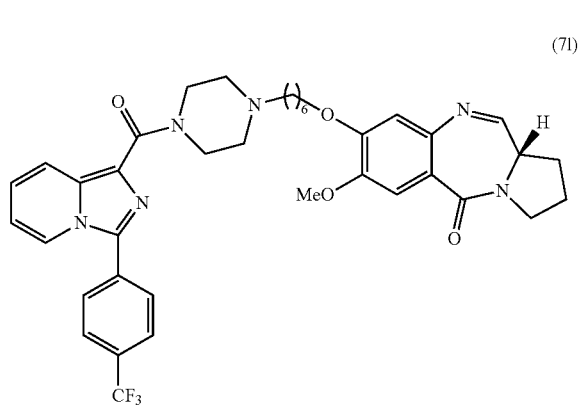
(7l)
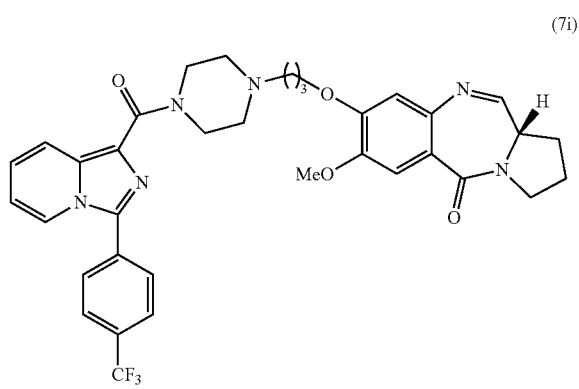
(7i)
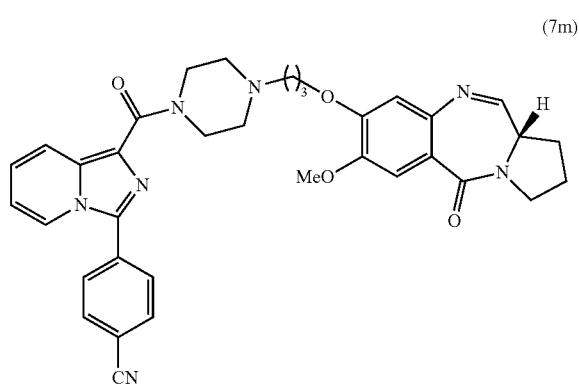
(7m)

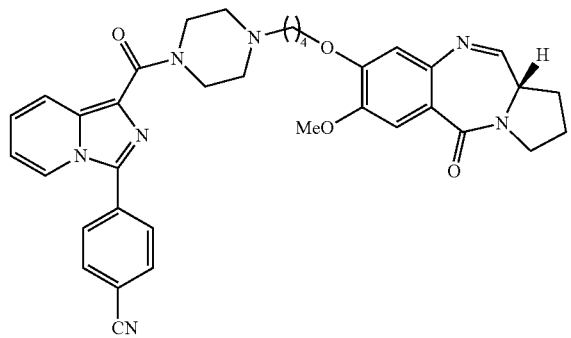
(7n)
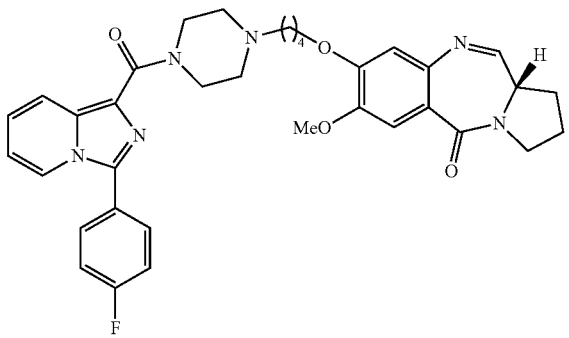
(7r)
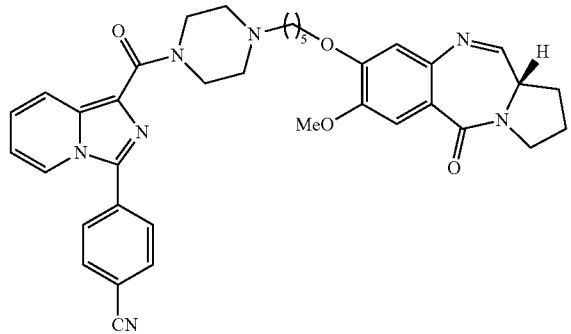
(7o)
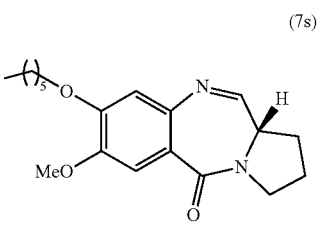
(7s)
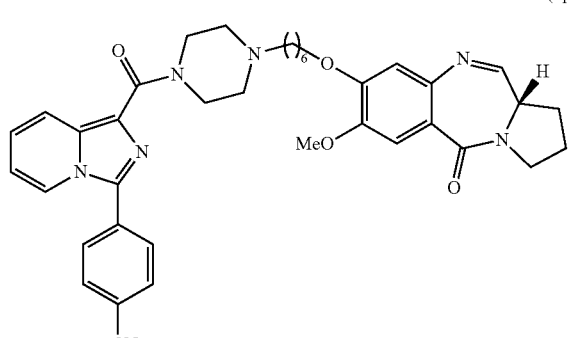
(7p)
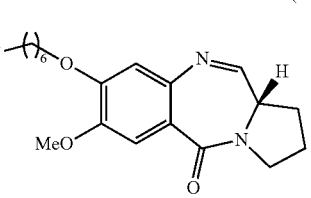
(7t)
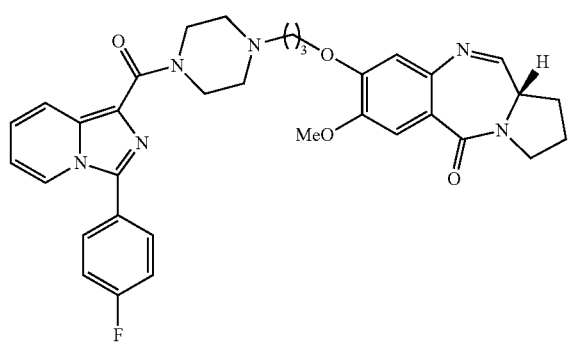
(7q)
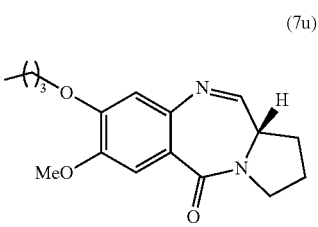
(7u)

-continued (7v)
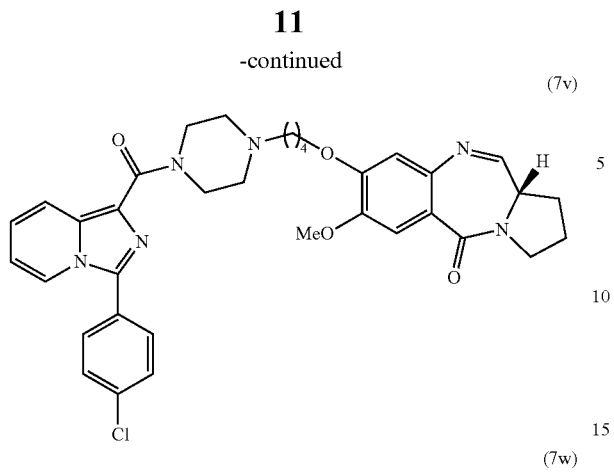

(7w)

(7x)

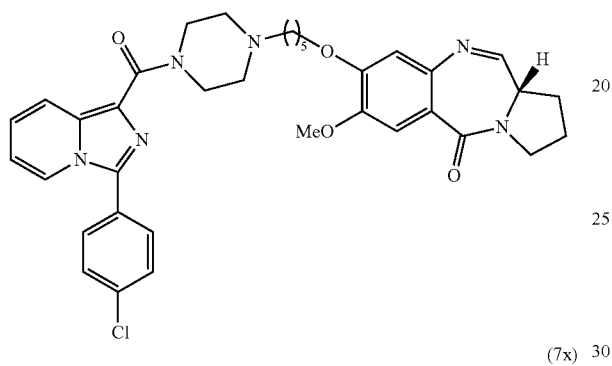

Yet another embodiment of the present invention provides a process for the preparation of pyrrolo[2,1-c][1,4]benzodiazepine linked imidazo[1,5-a]pyridine conjugates attached through a piperazine moiety and different alkane spacers of general formula 7 comprising the steps of:
a. reacting compound of formula 2 with compound of formula 4 in the ratio ranging between 1:1 ratio in the presence of $K_2CO_3$ in acetone solvent at refluxing temperature in the range of 56 to 60° C. to obtain the resultant nitro compound of formula 5;

2a-d
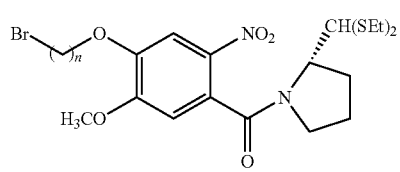

2a (n = 3) 2b (n = 4)
2c (n = 5) 2d (n = 6)

-continued 4 a-f
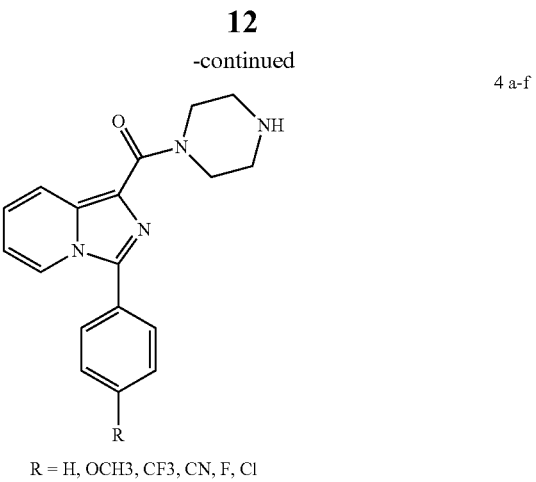

R = H, OCH3, CF3, CN, F, Cl 5 a-x
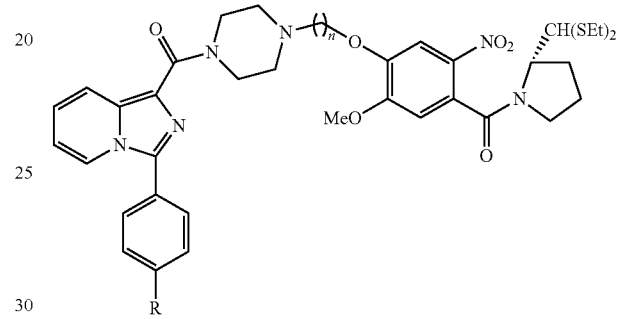

R = H, OCH3, CF3, CN, F, Cl
n = 3, 4, 5 and 6 b. reducing the nitro compound of formula 5 as obtained in step (a) with $SnCl_2 \cdot 2H_2O$ (1:3 ratio) in methanol solvent at temperature in the range of 66 to 70° C. to obtain amino compound of formula 6;

6 a-x
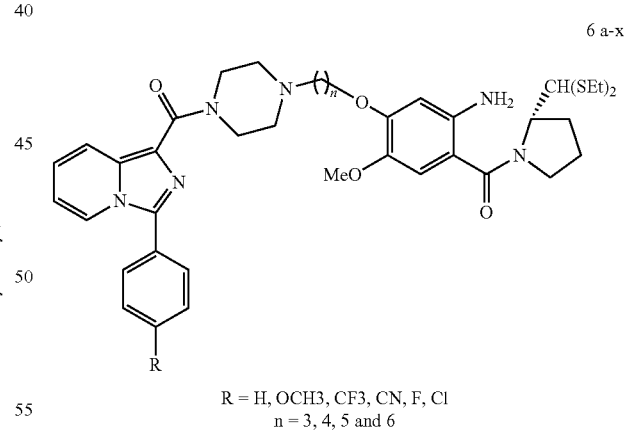

R = H, OCH3, CF3, CN, F, Cl
n = 3, 4, 5 and 6 c. reacting the amino compound of formula 6 as obtained in step (b) with a deprotecting agent $HgCl_2$ in acetonitrile-water (MeCN:$H_2O$ 4:1 ratio) by known method to obtain the desired compound of formula 7.

In yet another embodiment of the present invention, said compounds exhibiting $\Delta T_m$ value in the range of 4.9 to 10° C. after incubation at 37° C. for 0 to 18 hrs.

In yet another embodiement of the present invention, said compounds shows in-vitro anticancer activity against human tumor cells derived from five cancer types selected from the group consisting of breast cancer cell line (MCF-7), cervical cancer cell line (Hela), mouse melanoma cancer cell line (B16), lung cancer cell line (A549) and liver cancer cell line (Hepg2).

In yet another embodiement of the present invention, the compound 7a exhibiting in-vitro cytotoxicity in breast cancer cell line (MCF-7), cervical cancer cell line (Hela), mouse melanoma cancer cell line (B16), lung cancer cell line (A549) and liver cancer cell line (Hepg2) and there IC50 values are 1.2, 2.1, 2.8, 7.1 and 2.7 µM respectively. In yet another embodiement of the present invention, the compound 7b exhibiting in-vitro cytotoxicity in breast cancer cell line (MCF-7), cervical cancer cell line (Hela), mouse melanoma cancer cell line (B16), lung cancer cell line (A549) and liver cancer cell line (Hepg2) and there IC50 values are 2.87, 1.24, 2.67, 15.9 and 2.83 µM respectively.

In yet another embodiement of the present invention, the compound 7c exhibiting in-vitro cytotoxicity in breast cancer cell line (MCF-7), cervical cancer cell line (Hela), mouse melanoma cancer cell line (B16) and liver cancer cell line (Hepg2) and there IC50 values are 2.12, 1.66, 1.87 and 2.7 µM respectively.

In yet another embodiement of the present invention, the compound 7d exhibiting in-vitro cytotoxicity in breast cancer cell line (MCF-7), cervical cancer cell line (Hela), mouse melanoma cancer cell line (B16), lung cancer cell line (A549) and liver cancer cell line (Hepg2) and there IC50 values are 3.31, 3.97, 1.49, 12.4 and 3.06 µM respectively.

In yet another embodiement of the present invention, the compound 7e exhibiting in-vitro cytotoxicity in breast cancer cell line (MCF-7), cervical cancer cell line (Hela), mouse melanoma cancer cell line (B16), lung cancer cell line (A549) and liver cancer cell line (Hepg2) and there IC50 values are 2.26, 6.98, 2.7, 14.6 and 12.87 µM respectively.

In yet another embodiement of the present invention, the compound 7f exhibiting in-vitro cytotoxicity in breast cancer cell line (MCF-7), cervical cancer cell line (Hela), mouse melanoma cancer cell line (B16), lung cancer cell line (A549) and liver cancer cell line (Hepg2) and there IC50 values are 3.84, 3.82, 1.94, 13.6 and 1.72 µM respectively.

In yet another embodiement of the present invention, the compound 7g exhibiting in-vitro cytotoxicity in breast cancer cell line (MCF-7), cervical cancer cell line (Hela), mouse melanoma cancer cell line (B16), lung cancer cell line (A549) and liver cancer cell line (Hepg2) and there IC50 values are 1.16, 3.16, 3.02, 6.5 and 4.55 µM respectively.

In yet another embodiement of the present invention, the compound 7h exhibiting in-vitro cytotoxicity in breast cancer cell line (MCF-7), cervical cancer cell line (Hela), mouse melanoma cancer cell line (B16), lung cancer cell line (A549) and liver cancer cell line (Hepg2) and there IC50 values are 3.70, 6.97, 2.40, 33.0 and 2.69 µM respectively.

In still another embodiement of the present invention, the compound 7i exhibiting in-vitro cytotoxicity in breast cancer cell line (MCF-7), cervical cancer cell line (Hela), mouse melanoma cancer cell line (B16), lung cancer cell line (A549) and liver cancer cell line (Hepg2) and there IC50 values are 3.96, 1.46, <0.34, 11.4 and 1.48 µM respectively.

In yet another embodiement of the present invention, the compound 7j exhibiting in-vitro cytotoxicity in breast cancer cell line (MCF-7), Cervical cancer cell line (Hela), mouse melanoma cancer cell line (B16), lung cancer cell line (A549) and liver cancer cell line (Hepg2) and there IC50 values are 1.79, 4.43, 7.26, 7.0 and 1.27 µM respectively.

In yet another embodiement of the present invention, the compound 7k exhibiting in-vitro cytotoxicity in breast cancer cell line (MCF-7), Cervical cancer cell line (Hela), mouse melanoma cancer cell line (B16), lung cancer cell line (A549) and liver cancer cell line (Hepg2) and there IC50 values are 1.33, 0.86, 1.95, 8.0 and 1.12 µM respectively.

In still another embodiement of the present invention, the compound 7l exhibiting in-vitro cytotoxicity in breast cancer cell line (MCF-7), cervical cancer cell line (Hela), mouse melanoma cancer cell line (B16), lung cancer cell line (A549) and liver cancer cell line (Hepg2) and there IC50 values are 2.97, 3.97, 1.41, 12.14 and 2.0 µM respectively.

DETAILED DESCRIPTION OF THE INVENTION

The precursors [4-(n-bromoalkoxy)-5-methoxy-2-nitrophenyl]2-[di(ethylsulfanyl)methyl]tetrahydro-1H-1-pyrrolylmethanone of formula 2a-d (Kamal et al. *J. Med. Chem,* 2002, 45, 4679. *Bioorg. Med. Chem. Lett.* 2007, 19, 5345. *Bioorg. Med. Chem. Lett.* 2007, 19, 5345. *Bioorg. Med. Chem. Lett.* 2008, 18, 1468.) have been synthesized by known literature methods. The imidazopyridine precursors 4a-f have been prepared by cyclisation of ethyl 2-[(4-substitutedbenzoyl)amino]-2-(2-pyridyl)acetate, de-esterification, reaction with Boc protected piperazine, followed by deprotection.

These new analogues 7(a-x) of pyrrolo[2,1-c][1,4]benzodiazepine hybrids linked at C-8 position have shown promising DNA binding activity and efficient anticancer activity in various cell lines. The molecules synthesized are of massive biological significance with potential sequence selective DNA-binding property. General process for the preparation of compound of general formula 7 as illustrated in Scheme 1 is given below:

The ether linkage at C-8 position of DC-81 intermediates with imidazopyridine moieties.
1) Refluxing the reaction mixtures for 48 h.
2) Synthesis of C-8 linked PBD antitumour antibiotic hybrid imines.
3) Purification by column chromatography using different solvents like ethyl acetate, hexane, chloroform and methanol.

EXAMPLES

The following examples are given by way of illustration of the working of the invention in actual practice and therefore should not be construed to limit the scope of present invention.

Example 1

To a solution of (3-phenylimidazo[1,5-a]pyridin-1-yl)(piperazino)methanone (4a) (306 mg, 1 mmol) in acetone (10 mL) was added anhydrous $K_2CO_3$ (552 mg, 4 mmol) and the (11aS)-8-(3-bromopropoxy)-7-methoxy-2,3,5,11a-tetrahydro-1H-benzo[e]pyrrolo[1,2-a]azepin-5-one (2a) (521 mg, 1 mmol). The reaction mixture was heated to reflux for 48 h. After completion of the reaction as indicated by TLC, potassium carbonate was removed by suction filtration and the solvent was removed under vacuum. The crude product thus obtained was purified by column chromatography using ethylacetate-hexane (8:2) as eluant to afford pure compound of 5a (560 mg, 75%).

$^1$H NMR (CDCl$_3$, 300 MHz): δ 1.35 (q, 6H, J=7.1, 6.4 Hz), 1.48-2.35 (m, 11H), 2.51-2.94 (m, 9H), 3.15-3.35 (m, 2H), 3.92 (s, 3H), 4.20 (t, 2H, J=6.0, 5.8 Hz), 4.65-4.75 (m, 1H) 4.86 (d, 1H, J=3.7 Hz), 6.75 (t, 1H, J=7.1, 6.4 Hz), 6.81 (s, 1H), 7.04 (t 1H, J=8.8, 6.9 Hz), 7.44-7.60 (m, 3H), 7.69 (s, 1H), 7.77 (d, 2H J=6.9 Hz), 8.28-8.34 (m, 2H).

ESIMS: m/z 747 (M$^+$+1).

To compound 5a (747 mg, 1 mmol) in methanol (20 mL) was added SnCl$_2$.2H$_2$O (1.125 g, 5 mmol) and refluxed for 5 h or until the TLC indicated that reaction was completed. The methanol was evaporated under vacuum, the aqueous layer was then carefully adjusted to pH 8 with 10% NaHCO$_3$ solution and then extracted with ethyl acetate and chloroform (2×30 mL and 2×30 mL). The combined organic phase was dried over Na$_2$SO$_4$ and evaporated under vacuum to afford the crude amino diethylthioacetal 6a (573 mg, 80%), which was used directly in the next step.

A solution of 6a (652 mg, 1 mmol), HgCl$_2$ (613 mg, 2.26 mmol) and CaCO$_3$ (246 mg, 2.46 mmol) in acetonitrile-water (4:1) was stirred slowly at 27° C. for 12 hours. The reaction mixture was diluted with ethyl acetate (30 mL) filtered through a celite pad. The clear organic supernatant was extracted with saturated 5% NaHCO$_3$ (20 mL), brine (20 mL) and the combined organic phase was dried (Na$_2$SO$_4$). The organic layer was evaporated under vacuum and purified by column chromatography using MeOH—CHCl$_3$ (4%) to give compound 7a (355 mg, 60%). This material was repeatedly evaporated from CHCl$_3$ in vacuum to generate the imine form.

$^1$H NMR (CDCl$_3$, 300 MHz): δ 0.81-0.90 (m, 3H), 1.19-1.33 (m, 3H), 1.99-2.11 (m, 3H), 2.25-2.37 (m, 1H), 2.25-2.63 (m, 6H), 3.50-3.85 (m, 3H), 3.93 (s, 3H), 4.04-4.22 (m, 2H), 6.69 (t, 1H, J=7.5, 6.0 Hz), 6.79 (s, 1H), 6.97 (dd, 1H, J=6.7, 5.2 Hz), 7.40-7.55 (m, 4H), 7.60 (d, 1H, J=4.5 Hz), 7.74 (dd, 2H, J=6.7, 5.2 Hz), 8.25-8.35 (m, 2H).

ESIMS: m/z 593 (M$^+$+1).

Example 2

To a solution of (3-phenylimidazo[1,5-a]pyridin-1-yl)(piperazino)methanone (4a) (306 mg, 1 mmol) in acetone (10 mL) was added anhydrous K$_2$CO$_3$ (552 mg, 4 mmol) and (11aS)-8-(4-bromobutoxy)-7-methoxy-2,3,5,11a-tetrahydro-1H-benzo[e]pyrrolo[1,2-a]azepin-5-one (2b) (535 mg, 1 mmol). The reaction mixture was heated to reflux for 48 h. After completion of the reaction as indicated by TLC, potassium carbonate was removed by suction filtration and the solvent was removed under vacuum. The crude product thus obtained was purified by column chromatography using ethylacetate-hexane (8:2) as eluant to afford pure compound of 5b (570 mg) 75%

$^1$H NMR (CDCl$_3$, 300MHz): δ 1.33 (q, 6H, J=8.3, 7.5 Hz), 1.70-2.33 (m, 11H), 2.46-2.86 (m, 10H), 3.16-3.31 (m, 2H), 3.93 (s, 3H), 4.12 (t, 2H, J=6.0 Hz), 4.61-4.70 (m, 1H), 4.81 (d, 1H, J=3.7 Hz), 6.70 (t, 1H, J=6.7 Hz), 6.76 (s, 1H), 6.99 (dd, 1H, J=7.5, 6.7 Hz), 7.42-7.55 (m, 3H), 7.62 (s, 1H), 7.72 (d, 2H, J=7.5 Hz), 8.27 (d, 1H, J=7.5 Hz), 8.33 (d, 1H, J=9.0 Hz),

ESIMS: m/z 761 (M$^+$).

To compound 5b (761 mg, 1 mmol) in methanol (20 mL) was added SnCl$_2$.2H$_2$O (1.125 g, 5 mmol) and refluxed for 5 h or until the TLC indicated that reaction was completed. The methanol was evaporated under vacuum, the aqueous layer was then carefully adjusted to pH 8 with 10% NaHCO$_3$ solution and then extracted with ethyl acetate and chloroform (2×30 mL and 2×30 mL). The combined organic phase was dried over Na$_2$SO$_4$ and evaporated under vacuum to afford the crude amino diethylthioacetal 6b (548 mg, 75%), which was used directly in the next step.

A solution of 6b (731 mg, 1 mmol), HgCl$_2$ (613 mg, 2.26 mmol) and CaCO$_3$ (246 mg, 2.46 mmol) in acetonitrile-water (4:1) was stirred slowly at 27° C. for 12 hours. The reaction mixture was diluted with ethyl acetate (30 mL) filtered through a celite pad. The clear organic supernatant was extracted with saturated 5% NaHCO$_3$ (20 mL), brine (20 mL) and the combined organic phase was dried (Na$_2$SO$_4$). The organic layer was evaporated under vacuum and purified by column chromatography using MeOH—CHCl$_3$ (5%) to give compound 7b (363 mg, 60%). This material was repeatedly evaporated from CHCl$_3$ in vacuum to generate the imine form.

$^1$H NMR (CDCl$_3$, 500MHz): δ 1.69-1.93 (m, 3H), 1.84-1.94 (m, 2H), 1.17-2.10 (m, 5H), 2.24-2.35 (m, 2H), 2.50 (t, 2H J=7.8 Hz), 2.62-2.66 (m, 6H), 3.52-3.59 (m, 1H), 3.68-3.82 (m, 2H), 3.91 (s, 3H), 4.00-4.15 (m, 2H), 6.71 (t, 1H, J=7.8, 5.8 Hz), 6.79 (s, 1H), 6.97-7.01 (m, 1H), 7.44-7.54 (m, 4H), 7.64 (d, 1H, J=3.9 Hz), 7.74 (d, 2H, J=7.8 Hz), 8.28 (t, 2H, J=9.7, 7.8 Hz).

ESIMS: m/z 607 (M$^+$+1).

Example 3

To a solution of (3-phenylimidazo[1,5-a]pyridin-1-yl)(piperazino)methanone (4a) (306 mg, 1 mmol) in acetone (10 mL) was added anhydrous K$_2$CO$_3$ (552 mg, 4 mmol) and the (11aS)-8-[(5-bromopentyl)oxy]-7-methoxy-2,3,5,11a-tetrahydro-1H-benzo[e]pyrrolo[1,2-a]azepin-5-one (2c) (549 mg, 1 mmol). The reaction mixture was heated to reflux for 48 h. After completion of the reaction as indicated by TLC, potassium carbonate was removed by suction filtration and the solvent was removed under vacuum. The crude product thus obtained was purified by column chromatography using ethylacetate-hexane (8:2) as eluant to afford pure compound of 5c (581 mg, 75%).

$^1$H NMR (CDCl$_3$, 300 MHz): δ 1.34 (q, 6H, J=7.9, 7.5 Hz), 1.44-2.36 (m, 13H), 2.40-2.86 (m, 11H), 3.15-3.32 (m, 2H), 3.93 (s, 3H), 4.08 (t, 2H J=6.42, 6.23 Hz), 4.61-4.72 (m, 1H), 4.81 (d, 1H J=3.5 Hz), 6.70 (t, 1H, J=6.4, 6.2 Hz), 6.76 (s, 1H), 6.99 (dd, 1H, J=6.4, 6.2 Hz), 7.41-7.57 (m, 3H), 7.61 (s, 1H), 7.73 (d, 2H, J=6.9 Hz), 8.28 (d, 1H, J=6.9 Hz), 8.32 (d, 1H, J=9.0 Hz).

ESIMS: m/z 775 (M$^+$+1).

To compound 5c (775 mg, 1 mmol) in methanol (20 mL) was added SnCl$_2$.2H$_2$O (1.125 g, 5 mmol) and refluxed for 5 h or until the TLC indicated that reaction was completed. The methanol was evaporated under vacuum, the aqueous layer was then carefully adjusted to pH 8 with 10% NaHCO$_3$ solution and then extracted with ethyl acetate and chloroform (2×30 mL and 2×30 mL). The combined organic phase was dried over Na$_2$SO$_4$ and evaporated under vacuum to afford the crude amino diethyl thioacetal 6c (596 mg, 80%), which was used directly in the next step.

A solution of 6c (745 mg, 1 mmol), HgCl$_2$ (613 mg, 2.26 mmol) and CaCO$_3$ (246 mg, 2.46 mmol) in acetonitrile-water (4:1) was stirred slowly at 27° C. for 12 hours. The reaction mixture was diluted with ethyl acetate (30 mL) filtered through a celite pad. The clear organic supernatant was extracted with saturated 5% NaHCO$_3$ (20 mL), brine (20 mL) and the combined organic phase was dried (Na$_2$SO$_4$). The organic layer was evaporated under vacuum and purified by column chromatography using MeOH—CHCl$_3$ (4%) to give compound 7c (372 mg, 60%). This material was repeatedly evaporated from CHCl$_3$ in vacuum to generate the imine form.

$^1$H NMR (CDCl$_3$, 500 MHz): δ 1.53-1.78 (m, 8H), 1.82-1.91 (m, 2H), 1.98-2.05 (m, 2H), 2.23-2.42 (m, 4H), 2.55 (s, 4H), 3.50-3.85 (m, 3H), 3.92 (s, 3H), 3.98-4.11 (m, 2H), 6.69 (t, 1H, J=5.7, 7.7 Hz), 6.73 (s, 1H), 6.97 (t, 1H, J=7.7 Hz), 7.43-7.46 (m, 2H), 7.52 (t, 2H, J=7.7 Hz), 7.60 (d, 1H, J=3.8 Hz), 7.74 (d, 2H, J=7.7 Hz), 8.27 (d, 1H, J=7.7 Hz), 8.32 (d, 1H, J=7.7 Hz).

ESIMS: m/z 621 (M$^+$+1).

Example 4

To a solution of (3-phenylimidazo[1,5-a]pyridin-1-yl)(piperazino)methanone (4a) (306 mg, 1 mmol) in acetone (10 mL) was added anhydrous $K_2CO_3$ (552 mg, 4 mmol) and the (11aS)-8-[(6-bromohexyl)oxy]-7-methoxy-2,3,5,11a-tetrahydro-1H-benzo[e]pyrrolo[1,2-a]azepin-5-one (2d) (563 mg, 1 mmol). The reaction mixture was heated to reflux for 48 h. After completion of the reaction as indicated by TLC, potassium carbonate was removed by suction filtration and the solvent was removed under vacuum. The crude product thus obtained was purified by column chromatography using ethylacetate-hexane (8:2) as eluant to afford pure compound of 5d (552 mg, 70%).

$^1$H NMR ($CDCl_3$, 300 MHz): δ 1.20-1.28 (m, 2H), 1.36 (q, 6H, J=7.5, 6.7 Hz), 1.40-1.68 (m, 3H), 1.73-2.39 (m, 9H), 2.40-2.88 (m, 12H), 3.15-3.31 (m, 2H), 3.93 (s, 3H), 4.01-4.13 (m, 2H), 4.57-4.71 (m, 1H), 4.81 (d, 1H J=3.7 Hz), 6.70 (t, 1H, J=7.5, 6.0 Hz), 6.75 (s, 1H), 7.00 (dd, 1H, J=6.7, 6.0 Hz), 7.40-7.56 (m, 3H), 7.61 (s, 1H), 7.70-7.75 (m, 2H), 8.27 (d, 1H, J=6.7 Hz), 8.34 (d, 1H, J=9.0 Hz).

ESIMS: m/z 789 ($M^+$+1).

To compound 5d (789 mg, 1 mmol) in methanol (20 mL) was added $SnCl_2.2H_2O$ (1.125 g, 5 mmol) and refluxed for 5 h or until the TLC indicated that reaction was completed. The methanol was evaporated under vacuum; the aqueous layer was then carefully adjusted to pH 8 with 10% $NaHCO_3$ solution and then extracted with ethyl acetate and chloroform (2×30 mL and 2×30 mL). The combined organic phase was dried over $Na_2SO_4$ and evaporated under vacuum to afford the crude amino diethyl thioacetal 6d (607 mg, 80%), which was used directly in the next step.

A solution of 6d (759 mg, 1 mmol), $HgCl_2$ (613 mg, 2.26 mmol) and $CaCO_3$ (246 mg, 2.46 mmol) in acetonitrile-water (4:1) was stirred slowly at 27° C. for 12 hours. The reaction mixture was diluted with ethyl acetate (30 mL) filtered through a celite pad. The clear organic supernatant was extracted with saturated 5% $NaHCO_3$ (20 mL), brine (20 mL) and the combined organic phase was dried ($Na_2SO_4$). The organic layer was evaporated under vacuum and purified by column chromatography using $MeOH$—$CHCl_3$ (5%) to give compound 7d (348 mg, 55%). This material was repeatedly evaporated from $CHCl_3$ in vacuum to generate the imine form.

$^1$H NMR ($CDCl_3$, 300 MHz): δ 1.26-1.33 (m, 3H), 1.35-1.77 (m, 7H), 1.81-1.95 (m, 1H), 1.99-2.11 (m, 1H), 2.25-2.43 (m, 3H), 2.53 (s, 3H), 3.38-3.86 (m, 2H), 3.93 (s, 3H), 3.97-4.13 (m, 1H), 6.67-6.76 (m, 2H), 6.98 (dd, 1H, J=6.6, 6.4 Hz), 7.41-7.57 (m, 4H), 7.61 (d, 1H, J=4.1 Hz), 7.73 (d, 2H, J=6.9 Hz), 8.32 (dd, 2H, J=9.0, 8.1 Hz).

ESIMS: m/z 635 ($M^+$+1).

Example 5

To a solution of [3-(4-methoxyphenyl)imidazo[1,5-a]pyridin-1-yl](piperazino)methanone (4b) (336 mg, 1 mmol) in acetone (10 mL) was added anhydrous $K_2CO_3$ (552 mg, 4 mmol) and (11aS)-8-(3-bromopropoxy)-7-methoxy-2,3,5,11a-tetrahydro-1H-benzo[e]pyrrolo[1,2-a]azepin-5-one (2a) (521 mg, 1 mmol). The reaction mixture was heated to reflux for 48 h. After completion of the reaction as indicated by TLC, potassium carbonate was removed by suction filtration and the solvent was removed under vacuum. The crude product thus obtained was purified by column chromatography using ethylacetate-hexane (8:2) as eluant to afford pure compound of 5e (621 mg, 80%).

$^1$H NMR ($CDCl_3$, 300 MHz): δ 1.19-1.29 (m, 2H), 1.34 (q, 6H, J=7.5, 7.3 Hz), 1.73-2.35 (m, 8H), 2.62-2.87 (m, 10H), 3.14-3.32 (m, 2H), 3.88 (s, 3H), 3.93 (s, 3H), 4.18 (t, 2H J=5.8, 5.6 Hz), 4.61-4.69 (m, 1H), 4.82 (d, 1H, J=3.7 Hz), 6.68 (t, 1H, J=6.6, 6.4 Hz), 6.76 (s, 1H), 6.97 (dd, 1H, J=6.7, 6.6 Hz), 7.00 (d, 2H, J=8.6 Hz), 7.25 (s, 1H), 7.63 (d, 2H, J=6.9 Hz), 8.19 (d, 1H, J=7.1 Hz), 8.31 (d, 1H, J=9.0 Hz).

ESIMS: m/z 777 ($M^+$+1).

To compound 5e (777 mg, 1 mmol) in methanol (20 mL) was added $SnCl_2.2H_2O$ (1.125 g, 5 mmol) and refluxed for 5 h or until the TLC indicated that reaction was completed. The methanol was evaporated under vacuum, the aqueous layer was then carefully adjusted to pH 8 with 10% $NaHCO_3$ solution and then extracted with ethyl acetate and chloroform (2×30 mL and 2×30 mL). The combined organic phase was dried over $Na_2SO_4$ and evaporated under vacuum to afford the crude amino diethylthioacetal 6e which was used directly in the next step.

A solution of 6e (747 mg, 1 mmol), $HgCl_2$ (613 mg, 2.26 mmol) and $CaCO_3$ (246 mg, 2.46 mmol) in acetonitrile-water (4:1) was stirred slowly at 27° C. for 12 hours The reaction mixture was diluted with ethyl acetate (30 mL) filtered through a celite pad. The clear organic supernatant was extracted with saturated 5% $NaHCO_3$ (20 mL), brine (20 mL) and the combined organic phase was dried ($Na_2SO_4$). The organic layer was evaporated under vacuum and purified by column chromatography using $MeOH$—$CHCl_3$ (4%) to give compound 7e (311 mg, 50%). This material was repeatedly evaporated from $CHCl_3$ in vacuum to generate the imine form.

$^1$H NMR ($CDCl_3$, 300 MHz): δ 1.20-1.36 (m, 2H), 1.57-2.18 (m, 7H), 2.22-2.39 (m, 2H), 2.58 (s, 4H), 3.38-3.84 (m, 2H), 3.88 (s, 3H), 3.93 (s, 3H), 4.01-4.29 (m, 4H), 6.66 (t, 1H, J=6.7, 6.6 Hz), 6.80 (s, 1H), 6.95 (dd, 1H, J=6.9, 6.7 Hz), 7.00 (d, 2H, J=8.4 Hz), 7.44 (s, 1H), 7.62 (d, 1H, J=4.3 Hz), 7.67 (d, 2H, J=8.4 Hz), 8.19 (d, 1H, J=6.9 Hz), 8.28 (d, 1H, J=9.2 Hz).

ESIMS: m/z 623 ($M^+$+1).

Example 6

To a solution of [3-(4-methoxyphenyl)imidazo[1,5-a]pyridin-1-yl](piperazino)methanone (4b) (336 mg, 1 mmol) in acetone (10 mL) was added anhydrous $K_2CO_3$ (552 mg, 4 mmol) and the (11aS)-8-(4-bromobutoxy)-7-methoxy-2,3,5,11a-tetrahydro-1H-benzo[e]pyrrolo[1,2-a]azepin-5-one (2b) (535 mg, 1 mmol). The reaction mixture was heated to reflux for 48 h. After completion of the reaction as indicated by TLC, potassium carbonate was removed by suction filtration and the solvent was removed under vacuum. The crude product thus obtained was purified by column chromatography using ethylacetate-hexane (8:2) as eluant to afford pure compound of 5f (593 mg, 75%).

$^1$H NMR ($CDCl_3$, 300 MHz): δ 1.18-1.29 (m, 2H), 1.36 (q, 6H, J=7.5 Hz), 1.69-2.34 (m, 10H), 2.49-2.88 (m, 10H), 3.13-3.31 (m, 2H), 3.88 (s, 3H), 3.93 (s, 3H), 4.11 (t, 2H J=6.0 Hz), 4.61-4.70 (m, 1H), 4.82 (d, 1H, J=3.7 Hz), 6.68 (t, 1H, J=7.5, 6.0 Hz), 6.76 (s, 1H), 6.96 (dd, 1H, J=9.8, 6.7 Hz), 7.01 (d, 2H, J=9.0 Hz), 7.61 (s, 1H), 7.63 (d, 2H, J=9.0 Hz), 8.19 (d, 1H, J=6.7 Hz), 8.32 (d, 1H, J=9.0 Hz).

ESIMS: m/z 791 ($M^+$+1).

To compound 5f (791 mg, 1 mmol) in methanol (20 mL) was added $SnCl_2.2H_2O$ (1.125 g, 5 mmol) and refluxed for 5 h or until the TLC indicated that reaction was completed. The methanol was evaporated under vacuum, the aqueous layer was then carefully adjusted to pH 8 with 10% $NaHCO_3$ solution and then extracted with ethyl acetate and chloroform (2×30 mL and 2×30 mL). The combined organic phase was dried over $Na_2SO_4$ and evaporated under vacuum to afford the crude amino diethylthioacetal 6f which was used directly in the next step.

A solution of 6f (761 mg, 1 mmol), $HgCl_2$ (613 mg, 2.26 mmol) and $CaCO_3$ (246 mg, 2.46 mmol) in acetonitrile-water (4:1) was stirred slowly at 27° C. for 12 hours. The reaction mixture was diluted with ethyl acetate (30 mL) filtered through a celite pad. The clear organic supernatant was extracted with saturated 5% $NaHCO_3$ (20 mL), brine (20 mL) and the combined organic phase was dried ($Na_2SO_4$). The organic layer was evaporated under vacuum and purified by column chromatography using MeOH—$CHCl_3$ (5%) to give compound 7f (318 mg, 50%). This material was repeatedly evaporated from $CHCl_3$ in vacuum to generate the imine form.

$^1$H NMR ($CDCl_3$, 300 MHz): δ 1.20-1.35 (m, 1H), 1.64-2.13 (m, 8H), 2.22-2.61 (m, 8H), 3.42-3.84 (m, 2H), 3.88 (s, 3H), 3.92 (s, 3H), 3.98-4.28 (m, 4H), 6.66 (t, 1H, J=7.1, 6.4 Hz), 6.76 (s, 1H), 6.94 (dd, 1H, J=6.4, 2.6 Hz), 7.03 (d, 2H, J=8.8 Hz), 7.44 (s, 1H), 7.61 (d, 1H, J=4.3 Hz), 7.64 (d, 2H, J=8.6 Hz), 8.18 (d, 1H, J=7.1 'Hz), '8.28 (d, 1H, J=9.2 Hz).

ESIMS: m/z 637 ($M^+$+1).

Example 7

To a solution of [3-(4-methoxyphenyl)imidazo[1,5-a]pyridin-1-yl](piperazino)methanone (4b) (336 mg, 1 mmol) in acetone (10 mL) was added anhydrous $K_2CO_3$ (552 mg, 4 mmol) and the 2c (549 mg, 1 mmol). The reaction mixture was heated to reflux for 48 h. After completion of the reaction as indicated by TLC, potassium carbonate was removed by suction filtration and the solvent was removed under vacuum. The crude product thus obtained was purified by column chromatography using ethylacetate-hexane (8:2) as eluant to afford pure compound of 5g (563 mg, 70%).

$^1$H NMR ($CDCl_3$, 300 MHz): δ 1.33 (q, 6H, J=8.3, 7.5 Hz), 1.48-2.35 (m, 12H), 2.47-2.87 (m, 10H), 3.14-3.31 (m, 2H), 3.88 (s, 3H), 3.93 (s, 3H), 4.08 (t, 2H J=6.0 Hz), 4.61-4.71 (m, 1H), 4.81 (d, 1H, J=3.7 Hz), 6.68 (t, 1H, J=7.1, 6.2 Hz), 6.76 (s, 1H), 6.97 (dd, 1H, J=6.7, 6.4 Hz), 7.01 (d, 2H, J=8.6 Hz), 7.61-7.65 (m, 3H), 8.22 (d, 1H, J=7.1 Hz), 8.32 (d, 1H, J=9.2 Hz).

ESIMS: m/z 805 ($M^+$+1).

To compound 5g (805 mg, 1 mmol) in methanol (20 mL) was added $SnCl_2.2H_2O$ (1.125 g, 5 mmol) and refluxed for 5 h or until the TLC indicated that reaction was completed. The methanol was evaporated under vacuum, the aqueous layer was then carefully adjusted to pH 8 with 10% $NaHCO_3$ solution and then extracted with ethyl acetate and chloroform (2×30 mL and 2×30 mL). The combined organic phase was dried over $Na_2SO_4$ and evaporated under vacuum to afford the crude amino diethylthioacetal 6g which was used directly in the next step.

A solution of 6g (775 mg, 1 mmol), $HgCl_2$ (613 mg, 2.26 mmol) and $CaCO_3$ (246 mg, 2.46 mmol) in acetonitrile-water (4:1) was stirred slowly at 27° C. for 12 hours The reaction mixture was diluted with ethyl acetate (30 mL) filtered through a celite pad. The clear organic supernatant was extracted with saturated 5% $NaHCO_3$ (20 mL), brine (20 mL) and the combined organic phase was dried ($Na_2SO_4$). The organic layer was evaporated under vacuum and purified by column chromatography using MeOH—$CHCl_3$ (5%) to give compound 7g (390 mg, 60%). This material was repeatedly evaporated from $CHCl_3$ in vacuum to generate the imine form.

$^1$H NMR ($CDCl_3$, 300 MHz): δ1.22-1.34 (m, 1H), 1.46-1.77 (m, 8H), 1.82-1.97 (m, 2H), 1.99-2.09 (m, 2H), 2.25-2.42 (m, 4H), 2.54 (t, 4H, J=4.5 Hz), 3.43-3.83 (m, 2H), 3.88 (s, 3H), 3.93 (s, 3H), 3.96-4.14 (m, 2H), 6.66 (t, 1H, J=7.5, 6.0 Hz), 6.72 (s, 1H), 6.94 (dd, 1H, J=6.7, 5.2 Hz), 7.01 (d, 2H, J=9.0 Hz), 7.44 (s, 1H), 7.60 (d, 1H, J=4.5 Hz), 7.66 (d, 2H, J=9.0 Hz), 8.19 (d, 1H, J=6.7 Hz), 8.29 (d, 1H, J=9.0 Hz).

ESIMS: m/z 651 ($M^+$+1).

Example 8

To a solution of [3-(4-methoxyphenyl)imidazo[1,5-a]pyridin-1-yl](piperazino)methanone (4b) (336 mg, 1 mmol) in acetone (10 mL) was added anhydrous $K_2CO_3$ (552 mg, 4 mmol) and the 2d (563 mg, 1 mmol). The reaction mixture was heated to reflux for 48 h. After completion of the reaction as indicated by TLC, potassium carbonate was removed by suction filtration and the solvent was removed under vacuum. The crude product thus obtained was purified by column chromatography using ethylacetate-hexane (8:2) as eluant to afford pure compound of 5h (614 mg, 75%).

$^1$H NMR ($CDCl_3$, 300 MHz): δ 1.18-1.67 (m, 18H), 1.71-2.36 (m, 8H), 2.63-3.07 (m, 6H), 3.15-3.33 (m, 2H), 3.89 (s, 3H), 3.94 (s, 3H), 4.02-4.13 (m, 2H), 4.59-4.70 (m, 1H), 4.81 (d, 1H, J=3.7 Hz), 6.69-6.79 (m, 2H), 7.02 (d, 3H, J=8.3 Hz), 7.58-7.64 (m, 3H), 8.21 (d, 1H, J=6.7 Hz), 8.28 (d, 1H, J=9.0 Hz).

ESIMS: m/z 819 ($M^+$+1).

To compound 5h (819 mg, 1 mmol) in methanol (20 mL) was added $SnCl_2.2H_2O$ (1.125 g, 5 mmol) and refluxed for 5 h or until the TLC indicated that reaction was completed. The methanol was evaporated under vacuum, the aqueous layer was then carefully adjusted to pH 8 with 10% $NaHCO_3$ solution and then extracted with ethyl acetate and chloroform (2×30 mL and 2×30 mL). The combined organic phase was dried over $Na_2SO_4$ and evaporated under vacuum to afford the crude amino diethylthioacetal 6h, which was used directly in the next step.

A solution of 6h (789 mg, 1 mmol), $HgCl_2$ (613 mg, 2.26 mmol) and $CaCO_3$ (246 mg, 2.46 mmol) in acetonitrile-water (4:1) was stirred slowly at 27° C. for 12 hours. The reaction mixture was diluted with ethyl acetate (30 mL) filtered through a celite pad. The clear organic supernatant was extracted with saturated 5% $NaHCO_3$ (20 mL), brine (20 mL) and the combined organic phase was dried ($Na_2SO_4$). The organic layer was evaporated under vacuum and purified by column chromatography using MeOH—$CHCl_3$ (5%) to give compound 7h (365 mg, 55%). This material was repeatedly evaporated from $CHCl_3$ in vacuum to generate the imine form.

$^1$H NMR ($CDCl_3$, 300 MHz): δ 1.21-1.62 (m, 9H), 1.81-1.93 (m, 2H), 1.98-2.10 (m, 2H), 2.25-2.41 (m, 4H), 2.53 (t, 4H, J=4.9, 4.7 Hz), 3.43-3.84 (m, 4H), 3.88 (s, 3H), 3.92 (s, 3H), 3.95-4.13 (m, 2H), 6.66 (t, 1H, J=6.2, 6.0 Hz), 6.73 (s, 1H), 6.94 (dd, 1H, J=6.4, 5.4 Hz), 7.01 (d, 2H, J=9.0 Hz), 7.43 (s, 1H), 7.61 (d, 1H, J=4.3 Hz), 7.65 (d, 2H, J=8.8 Hz), 8.20 (d, 1H, J=7.1 Hz), 8.30 (d, 1H, J=9.2 Hz).

ESIMS: m/z 666 ($M^+$+1).

Example 9

To a solution of piperazino3-[4-(trifluoromethyl)phenyl]imidazo[1,5-a]pyridin-1-ylmethanone (4c) (374 mg, 1 mmol) in acetone (10 mL) was added anhydrous $K_2CO_3$ (552 mg, 4 mmol) and the 2a (521 mg, 1 mmol). The reaction mixture was heated to reflux for 48 h. After completion of the reaction as indicated by TLC, potassium carbonate was removed by suction filtration and the solvent was removed under vacuum. The crude product thus obtained was purified by column chromatography using ethylacetate-hexane (8:2) as eluant to afford pure compound of 5i (611 mg, 75%).

$^1$H NMR (CDCl$_3$, 300 MHz): δ 1.10-1.29 (m, 1H), 1.35 (q, 6H, J=7.5, 7.3 Hz), 1.73-2.35 (m, 10H), 2.62-2.90 (m, 9H), 3.15-3.31 (m, 2H), 3.93 (s, 3H), 4.20 (t, 2H J=6.4, 6.0 Hz), 4.60-4.71 (m, 1H), 4.82 (d, 1H, J=3.7 Hz), 6.76 (s, 1H), 6.80 (dd, 1H, J=7.3, 6.9), 7.06 (dd, 1H, J=6.4, 5.4 Hz), 7.65 (s, 1H), 7.80 (d, 2H, J=8.3 Hz), 7.91 (d, 2H, J=8.1 Hz), 8.30 (d, 1H, J=7.3 Hz), 8.38 (d, 1H, J=9.2 Hz).

ESIMS: m/z 815 (M$^+$).

To compound 5i (815 mg, 1 mmol) in methanol (20 mL) was added SnCl$_2$.2H$_2$O (1.125 g, 5 mmol) and refluxed for 5 h or until the TLC indicated that reaction was completed. The methanol was evaporated under vacuum, the aqueous layer was then carefully adjusted to pH 8 with 10% NaHCO$_3$ solution and then extracted with ethyl acetate and chloroform (2×30 mL and 2×30 mL). The combined organic phase was dried over Na$_2$SO$_4$ and evaporated under vacuum to afford the crude amino diethylthioacetal 6i which was used directly in the next step.

A solution of 6i (785 mg, 1 mmol), HgCl$_2$ (613 mg, 2.26 mmol) and CaCO$_3$ (246 mg, 2.46 mmol) in acetonitrile-water (4:1) was stirred slowly at 27° C. for 12 hours The reaction mixture was diluted with ethyl acetate (30 mL) filtered through a celite pad. The clear organic supernatant was extracted with saturated 5% NaHCO$_3$ (20 mL), brine (20 mL) and the combined organic phase was dried (Na$_2$SO$_4$). The organic layer was evaporated under vacuum and purified by column chromatography using MeOH—CHCl$_3$ (5%) to give compound 7i (363 mg, 55%). This material was repeatedly evaporated from CHCl$_3$ in vacuum to generate the imine form.

$^1$H NMR (CDCl$_3$, 300 MHz): δ 0.81-0.93 (m, 3H), 1.21-1.38 (m, 3H), 1.45-1.66 (m, 3H), 1.98-2.16 (m, 3H), 2.25-2.39 (m, 1H), 2.58 (t, 4H, J=5.0, 4.7 Hz), 3.44-3.86 (m, 2H), 3.93 (s, 3H), 3.98-4.27 (m, 2H), 6.77 (dd, 1H, J=6.4, 6.2 Hz), 6.80 (s, 1H), 7.04 (dd, 1H, J=7.1, 6.4 Hz), 7.44 (s, 1H), 7.61 (d, 1H, J=4.3 Hz), 7.79 (d, 2H, J=8.1 Hz), 7.91 (d, 1H, J=8.1 Hz), 8.29 (d, 1H, J=7.1 Hz), 8.37 (d, 1H, J=9.2 Hz).

ESIMS: m/z 661 (M$^+$+1).

Example 10

To a solution of piperazino3-[4-(trifluoromethyl)phenyl] imidazo[1,5-a]pyridin-1-yl methanone (4c) (374 mg, 1 mmol) in acetone (10 mL) was added anhydrous K$_2$CO$_3$ (552 mg, 4 mmol) and 2b (535 mg, 1 mmol). The reaction mixture was heated to reflux for 48 h. After completion of the reaction as indicated by TLC, potassium carbonate was removed by suction filtration and the solvent was removed under vacuum. The crude product thus obtained was purified by column chromatography using ethylacetate-hexane (7:2) as eluant to afford pure compound of 5j (622 mg) 75%.

$^1$H NMR (CDCl$_3$, 300 MHz): δ 1.33 (q, 6H, J=7.5, 7.3 Hz), 1.68-2.36 (m, 12H), 2.48-2.88 (m, 10H), 3.12-3.31 (m, 2H), 3.93 (s, 3H), 4.06-4.19 (m, 2H), 4.61-4.71 (m, 1H), 4.81 (d, 1H, J=3.2 Hz), 6.72-6.82 (m, 2H), 7.04 (t, 1H, J=8.3, 7.1 Hz), 7.62 (s, 1H), 7.81 (d, 2H, J=8.1 Hz), 7.92 (d, 2H, J=7.9 Hz), 8.30 (d, 1H, J=7.1 Hz), 8.35 (d, 1H, J=8.8 Hz). ESIMS: m/z 844 (M$^+$+1).

To compound 5j (830 mg, 1 mmol) in methanol (20 mL) was added SnCl$_2$.2H$_2$O (1.125 g, 5 mmol) and refluxed for 5 h or until the TLC indicated that reaction was completed. The methanol was evaporated under vacuum; the aqueous layer was then carefully adjusted to pH 8 with 10% NaHCO$_3$ solution and then extracted with ethyl acetate and chloroform (2×30 mL and 2×30 mL). The combined organic phase was dried over Na$_2$SO$_4$ and evaporated under vacuum to afford the crude amino diethylthioacetal 6j (599 mg, 75%), which was used directly in the next step.

A solution of 6j (799 mg, 1 mmol), HgCl$_2$ (613 mg, 2.26 mmol) and CaCO$_3$ (246 mg, 2.46 mmol) in acetonitrile-water (4:1) was stirred slowly at 27° C. for 12 hours. The reaction mixture was diluted with ethyl acetate (30 mL) filtered through a celite pad. The clear organic supernatant was extracted with saturated 5% NaHCO$_3$ (20 mL), brine (20 mL) and the combined organic phase was dried (Na$_2$SO$_4$). The organic layer was evaporated under vacuum and purified by column chromatography using MeOH—CHCl$_3$ (5%) to give compound 7j (377 mg, 56%). This material was repeatedly evaporated from CHCl$_3$ in vacuum to generate the imine form.

$^1$H NMR (CDCl$_3$, 300 MHz): δ 0.83-0.98 (m, 2H), 1.19-1.36 (m, 2H), 1.64-1.80 (m, 2H), 1.85-2.11 (m, 4H), 2.24-2.36 (m, 2H), 2.46 (t, 2H, J=7.5, 6.7 Hz), 2.54-2.66 (t, 4H, J=4.5 Hz), 3.40-3.84 (m, 3H), 3.92 (s, 3H), 3.99-4.15 (m, 2H), 6.74-6.81 (m, 2H), 7.03 (dd, 1H, J=6.7 Hz), 7.44 (s, 1H), 7.61 (d, 1H, J=4.5 Hz), 7.77 (d, 2H, J=8.3 Hz), 7.90 (d, 2H, J=7.5 Hz), 8.28 (d, 1H, J=7.5 Hz), 8.35 (d, 1H, J=9.0 Hz).

ESIMS: m/z 675 (M$^+$+1).

Example 11

To a solution of piperazino3-[4-(trifluoromethyl)phenyl] imidazo[1,5-a]pyridin-1-yl methanone (4c) (374 mg, 1 mmol) in acetone (10 mL) was added anhydrous K$_2$CO$_3$ (552 mg, 4 mmol) and 2c (549 mg, 1 mmol). The reaction mixture was heated to reflux for 48 h. After completion of the reaction as indicated by TLC, potassium carbonate was removed by suction filtration and the solvent was removed under vacuum. The crude product thus obtained was purified by column chromatography using ethylacetate-hexane (7:2) as eluant to afford pure compound of 5k (590 mg, 70%).

$^1$H NMR (CDCl$_3$, 300 MHz): δ 1.33 (q, 6H, J=7.5 Hz), 1.46-2.36 (m, 13H), 2.46-2.89 (m, 11H), 3.14-3.34 (m, 2H), 3.93 (s, 3H), 4.08 (t, 2H, J=6.4, 6.0 Hz)), 4.60-4.72 (m, 1H), 4.82 (d, 1H, J=3.5 Hz), 6.72-6.82 (m, 2H), 7.06 (dd, 1H, J=6.7, 6.4 Hz), 7.61 (s, 1H), 7.81 (d, 2H, J=8.3 Hz), 7.89 (d, 2H, J=8.1 Hz), 8.31 (d, 1H, J=6.9 Hz), 8.36 (d, 1H, J=9.2 Hz).

ESIMS: m/z 829 (M$^+$).

To compound 5k (843 mg, 1 mmol) in methanol (20 mL) was added SnCl$_2$.2H$_2$O (1.125 g, 5 mmol) and refluxed for 5 h or until the TLC indicated that reaction was completed. The methanol was evaporated under vacuum; the aqueous layer was then carefully adjusted to pH 8 with 10% NaHCO$_3$ solution and then extracted with ethyl acetate and chloroform (2×30 mL and 2×30 mL). The combined organic phase was dried over Na$_2$SO$_4$ and evaporated under vacuum to afford the crude amino diethyl thioacetal 6k (650 mg, 80%), which was used directly in the next step.

A solution of 6k (813 mg, 1 mmol), HgCl$_2$ (613 mg, 2.26 mmol) and CaCO$_3$ (246 mg, 2.46 mmol) in acetonitrile-water (4:1) was stirred slowly at 27° C. for 12 hours. The reaction mixture was diluted with ethyl acetate (30 mL) filtered through a celite pad. The clear organic supernatant was extracted with saturated 5% NaHCO$_3$ (20 mL), brine (20 mL) and the combined organic phase was dried (Na$_2$SO$_4$). The organic layer was evaporated under vacuum and purified by column chromatography using MeOH—CHCl$_3$ (5%) to give compound 7k (378 mg, 55%). This material was repeatedly evaporated from CHCl$_3$ in vacuum to generate the imine form.

¹H NMR (CDCl₃, 500 MHz): δ 1.59 (d, 5H, J=24.2 Hz), 1.89 (d, 5H, J=76.4 Hz), 2.29 (d, 5H, J=50.3 Hz), 2.53 (s, 5H), 3.39-3.78 (m, 3H), 3.91 (s, 3H), 4.06 (d, 2H, J=27.0 Hz), 6.65-6.83 (m, 2H), 7.01 (s, 1H), 7.43 (s, 1H), 7.59 (s, 1H), 7.77 (d, 2H, J=7.4 Hz), 7.90 (d, 2H, J=7.4 Hz), 8.28 (d, 1H, J=6.5 Hz), 8.34 (d, 1H, J=9.3 Hz).

ESIMS: m/z 690 (M⁺+1).

Example 12

To a solution of piperazino3-[4-(trifluoromethyl)phenyl] imidazo[1,5-a]pyridin-1-yl methanone (4c) (374 mg, 1 mmol) in acetone (10 mL) was added anhydrous K₂CO₃ (552 mg, 4 mmol) and 2d (563 mg, 1 mmol). The reaction mixture was heated to reflux for 48 h. After completion of the reaction as indicated by TLC, potassium carbonate was removed by suction filtration and the solvent was removed under vacuum. The crude product thus obtained was purified by column chromatography using ethylacetate-hexane (7:3) as eluant to afford pure compound of 5l (685 mg, 80%).

¹H NMR (CDCl₃, 300 MHz): δ 1.17-1.70 (m, 14H), 1.72-2.17 (m, 6H), 2.39-2.89 (m, 12H), 3.13-3.33 (m, 2H), 3.94 (s, 3H), 4.07 (t, 2H J=6.2, 6.0 Hz), 4.60-4.72 (m, 1H), 4.81 (d, 1H, J=3.7 Hz), 6.72-6.83 (m, 2H), 7.05 (dd, 1H, J=9.0, 6.4 Hz), 7.61 (s, 1H), 7.81 (d, 2H, J=8.3 Hz), 7.92 (d, 2H, J=8.1 Hz), 8.29 (d, 1H, J=7.1 Hz), 8.37 (d, 1H, J=9.0 Hz). ESIMS: m/z 858 (M⁺+1).

To compound 5l (857 mg, 1 mmol) in methanol (20 mL) was added SnCl₂.2H₂O (1.125 g, 5 mmol) and refluxed for 5 h or until the TLC indicated that reaction was completed. The methanol was evaporated under vacuum; the aqueous layer was then carefully adjusted to pH 8 with 10% NaHCO₃ solution and then extracted with ethyl acetate and chloroform (2×30 mL and 2×30 mL). The combined organic phase was dried over Na₂SO₄ and evaporated under vacuum to afford the crude amino diethylthioacetal 6l which was used directly in the next step.

A solution of 6l (827 mg, 1 mmol), HgCl₂ (613 mg, 2.26 mmol) and CaCO₃ (246 mg, 2.46 mmol) in acetonitrile-water (4:1) was stirred slowly at 27° C. for 12 hours. The reaction mixture was diluted with ethyl acetate (30 mL) filtered through a celite pad. The clear organic supernatant was extracted with saturated 5% NaHCO₃ (20 mL), brine (20 mL) and the combined organic phase was dried (Na₂SO₄). The organic layer was evaporated under vacuum and purified by column chromatography using MeOH—CHCl₃ (4%) to give compound 7l (386 mg, 55%). This material was repeatedly evaporated from CHCl₃ in vacuum to generate the imine form.

¹H NMR (CDCl₃, 300 MHz): δ 1.20-1.65 (m, 13H), 1.81-1.95 (m, 2H), 1.98-2.13 (m, 2H), 2.24-2.45 (m, 3H), 2.49-2.62 (m, 3H), 3.45-3.86 (m, 2H), 3.93 (s, 3H), 3.97-4.14 (m, 2H), 6.71-6.80 (m, 2H), 7.03 (dd, 1H, J=6.6, 6.4 Hz), 7.43 (s, 1H), 7.60 (d, 1H, J=4.3 Hz), 7.79 (d, 2H, J=8.3 Hz), 7.91 (d, 2H, J=8.1 Hz), 8.29 (d, 1H, J=7.1 Hz), 8.37 (d, 1H, J=9.2 Hz).

ESIMS: m/z 704 (M⁺+1).

Biological Activity
DNA Binding Affinity of Imidazo [1,5-a]Pyridine Linked PBD Hybrids (7a-l)

Compounds have been subjected to thermal denaturation studies with duplex-form calf thymus DNA (CT-DNA) using a modification of a reported procedure (Newman, M. S. *Carcinog-compr. Surv.* 1976, 1, 203; (b) Hecht, S. S.; Loy, M.; Hoffman, *Carcinog-compr. Surv.* 1976, 1, 325). Working solutions in aqueous buffer (10 mM NaH₂PO₄/Na₂HPO₄, 1 mM Na₂EDTA, pH 7.00+0.01) containing CT-DNA (100 μm in phosphate) and the PBD (20 μm) have been prepared by addition of concentrated PBD solutions in DMSO to obtain a fixed [PBD]/[DNA] molar ratio of 1:5. The DNA-PBD solutions have been incubated at 37° C. for 0 and 18 h prior to analysis. Samples have been monitored at 260 nm using a Beckman DU-800 spectrophotometer fitted with high performance temperature controller, and heated at 1° C. min⁻¹ in the 40-110° C. range. DNA helix→coil transition temperatures ($T_m$) have been obtained from the maxima in the $d(A_{260})/dT$ derivative plots. Drug-induced alterations in DNA melting behavior are given by: $\Delta T_m = T_m(DNA+PBD) - T_m(DNA$ alone), where the $T_m$ value for the PBD-free CT-DNA is 69.1±0.01. The fixed [PBD]/[DNA] ratio used has not resulted in binding saturation of the host DNA duplex for any compound examined.

The DNA binding activity for these novel C8-linked imidazo[1,5-a]pyridine PBD hybrids has been examined by thermal denaturation studies using calf thymus (CT) DNA. Melting studies show that these compounds stabilize the thermal helix→coil or melting stabilization ($\Delta T_m$) ($\Delta Tm=Tm(DNA+PBD)-Tm(DNA$ alone)) for the CT-DNA duplex at pH 7.0, incubated at 37° C., where PBD/DNA molar ratio is 1:5. The data for the compounds 7a-l is included in Table 1 for comparison.

TABLE 1

Thermal denaturation data for imidazo[1,5-a]pyridine linked PBD hybrids with calf thymus (CT) DNA at a molar ratio of 1:5 in aqueous sodium phosphate buffer at pH 7 and having the following thermal denaturation data:

| | [PBD]:[DNA] | ($\Delta T_m$ ° C.)ᵃ after incubation at 37° C. for | |
|---|---|---|---|
| PBD hybrids | molar ratioᵇ | 0 h | 18 h |
| 7a | 1:5 | 6.0 | 8.9 |
| 7b | 1:5 | 6.0 | 8.9 |
| 7c | 1:5 | 7.0 | 9.0 |
| 7d | 1:5 | 7.0 | 8.0 |
| 7e | 1:5 | 4.9 | 8.8 |
| 7f | 1:5 | 5.9 | 9.9 |
| 7g | 1:5 | 5.9 | 9.9 |
| 7h | 1:5 | 5.9 | 8.9 |
| 7i | 1:5 | 5.9 | 8.8 |
| 7j | 1:5 | 6.9 | 10.0 |
| 7k | 1:5 | 7.9 | 10.0 |
| 7l | 1:5 | 7.0 | 8.8 |
| DC-81 | 1:5 | 0.3 | 0.7 |
| 4a | 1:5 | 1.0 | 1.2 |
| 4b | 1:5 | 1.1 | 1.2 |
| 4c | 1:5 | 0.1 | 0.4 |

ᵃFor CT-DNA alone at pH 7.00 ± 0.01, $T_m$ = 69.1° C. ± 0.01 (mean value from 10 separate determinations), all $\Delta T_m$ values are ± 0.1-0.2° C.
ᵇFor a 1:5 molar ratio of [PBD]/[DNA], where CT-DNA concentration = 100 μM and ligand concentration = 20 μM in aqueous sodium phosphate buffer [10 mM sodium phosphate + 1 mM EDTA, pH 7.00 ± 0.01].

Anticancer Activity

In vitro biological activity studies were carried out at the pharmacology division, IICT, Hyderabad. The compounds were evaluated for in vitro anticancer activity against five tumour cell lines derived from five cancer types (breast, cervix, mouse melanoma, lung and liver cancer) as shown in Table 2. For each compound, dose response curves for each cell line were measured at a minimum of five concentrations at 10 fold dilutions. A protocol of 48 h continuous drug exposure was used and a MTT assay was used to estimate cell viability or growth. The concentration causing 50% inhibition ($IC_{50}$) compared with the control was calculated. Compounds 7a-7l have been evaluated for their in vitro cytotoxicity in five cell lines from five human cancer types. The results are expressed as $IC_{50}$ determined relative to that of untreated control cells (Table-2).

TABLE 2

IC$_{50}$ (concentration in μM) values for the representative compounds 7(a-l) against human tumour cell lines.

| Cell type | MCF-7 | Hela | B16 | A549 | Hepg2 |
|---|---|---|---|---|---|
| 7a | 1.2 | 2.1 | 2.8 | 7.1 | 2.7 |
| 7b | 2.87 | 1.24 | 2.67 | 15.9 | 2.83 |
| 7c | 2.12 | 1.66 | 1.87 | NA | 3.86 |
| 7d | 3.31 | 3.97 | 1.49 | 12.4 | 3.06 |
| 7e | 2.26 | 6.98 | 2.7 | 14.6 | 12.8 |
| 7f | 3.84 | 3.82 | 1.94 | 13.6 | 1.72 |
| 7g | 1.16 | 3.16 | 3.02 | 6.5 | 4.55 |
| 7h | 3.70 | 6.97 | 2.40 | 33.0 | 2.69 |
| 7i | 3.96 | 1.46 | <0.34 | 11.4 | 1.48 |
| 7j | 1.79 | 4.43 | 7.26 | 7.0 | 1.27 |
| 7k | 1.33 | 0.86 | 1.95 | 8.0 | 1.12 |
| 7l | 2.97 | 3.79 | 1.41 | 12.14 | 2.0 |
| DC-81 | 2.19 | 2.14 | 1.83 | 0.38 | 2.2 |
| ADR | 1.6 | 0.13 | 0.34 | 2.9 | 1.85 |
| 4a | >100 | >100 | >100 | >100 | >100 |
| 4b | >100 | >100 | >100 | >100 | >100 |
| 4c | >100 | >100 | >100 | >100 | >100 |

Where ADR = adiramycin and DC-81 = pyrrolo[2,1-c][1,4]benzodiazepine

ADVANTAGES OF THE INVENTION

DNA alkylating agents have been widely used in cancer chemotherapy. These agents have several drawbacks including a lack of drug-specific affinity towards tumour cells. To overcome this problem, in the present invention the alkylating agents coupled with DNA minor groove binders. Moreover, the thermal denaturation study reveals that conjugates are more effective than their individual motiefs.

We claim:
1. Pyrrolo[2,1-c][1,4]benzodiazepine linked imidazo[1,5-a]pyridine conjugates of general formula 7

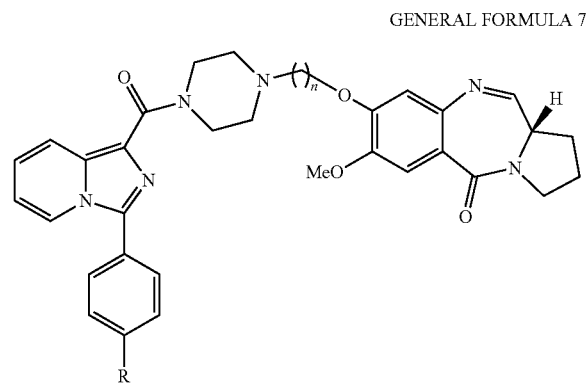

GENERAL FORMULA 7 wherein R represents H, OCH$_3$, CF$_3$, CN, F or Cl; and n=3, 4, 5 or 6.

2. The compound as claimed in claim 1, wherein chemical formula of the representative compounds of formula 7 are:
(11aS)-7-methoxy-8-(3-4-[(3-phenylimidazo[1,5-a]pyridin-yl)carbonyl]piperazino propoxy)-2,3,5,11a-tetrahydro-1H-benzo[e]pyrrolo[1,2-a]azepin-5-one (7a);
(11aS)-7-methoxy-8-(4-4-[(3-phenylimidazo[1,5-a]pyridin-yl)carbonyl]piperazino butoxy)-2,3,5,11a-tetrahydro-1H-benzo[e]pyrrolo[1,2-a]azepin-5-one (7b);
(11aS)-7-methoxy-8-[(5-4-[(3-phenylimidazo[1,5-a]pyridin-1-yl)carbonyl]piperazino pentyl)oxy]-2,3,5,11a-tetrahydro-1H-benzo[e]pyrrolo[1,2-a]azepin-5-one (7c);
(11aS)-7-methoxy-8-[(6-4-[(3-phenylimidazo[1,5-a]pyridin-1-yl)carbonyl]piperazino hexyl)oxy]-2,3,5,11a-tetrahydro-1H-benzo[e]pyrrolo[1,2-a]azepin-5-one (7d);
(11aS)-7-methoxy-8-[3-(4-[3-(4-methoxyphenyl)imidazo[1,5-a]pyridin-1-yl]carbonyl piperazino)propoxy]-2,3,5,11a-tetrahydro-1H-benzo[e]pyrrolo[1,2-a]azepin-5-one (7e);
(11aS)-7-methoxy-8-[4-(4-[3-(4-methoxyphenyl)imidazo[1,5-a]pyridin-1-yl]carbonyl piperazino)butoxy]-2,3,5,11a-tetrahydro-1H-benzo[e]pyrrolo[1,2-a]azepin-5-one (7f);
(11aS)-7-methoxy-8-[5-(4-[3-(4-methoxyphenyl)imidazo[1,5-a]pyridin-1-yl]carbonyl piperazino)pentyl]oxy-2,3,5,11a-tetrahydro-1H-benzo[e]pyrrolo[1,2-a]azepin-5-one (7g);
(11aS)-7-methoxy-8-[6-(4-[3-(4-methoxyphenyl)imidazo[1,5-a]pyridin-1-yl]carbonyl piperazino)hexyl]oxy-2,3,5,11a-tetrahydro-1H-benzo[e]pyrrolo[1,2-a]azepin-5-one (7h);
(11aS)-7-methoxy-8-3-[4-(3-[4-(trifluoromethyl)phenyl]imidazo[1,5-a]pyridin-1-yl carbonyl)piperazino]propoxy-2,3,5,11a-tetrahydro-1H-benzo[e]pyrrolo[1,2-a]azepin-5-one (7l);
(11aS)-7-methoxy-8-4-[4-(3-[4-(trifluoromethyl)phenyl]imidazo[1,5-a]pyridin-1-yl carbonyl)piperazino]butoxy-2,3,5,11a-tetrahydro-1H-benzo[e]pyrrolo[1,2-a]azepin-5-one (7j);
(11aS)-7-methoxy-8-(5-[4-(3-[4-(trifluoromethyl)phenyl]imidazo[1,5-a]pyridin-1-yl carbonyl)piperazino]pentyloxy)-2,3,5,11a-tetrahydro-1H-benzo[e]pyrrolo[1,2-a]azepin-5-one (7k);
(11aS)-7-methoxy-8-(6-[4-(3-[4-(trifluoromethyl)phenyl]imidazo[1,5-a]pyridin-1-yl carbonyl)piperazino]hexyloxy)-2,3,5,11a-tetrahydro-1H-benzo[e]pyrrolo[1,2-a]azepin-5-one (7l);
4-(1-[4-(3-[(11aS)-7-methoxy-5-oxo-2,3,5,11a-tetrahydro-1H-benzo[e]pyrrolo[1,2-a]azepin-8-yl]oxypropyl)piperazino]carbonylimidazo[1,5-a]pyridin-3-yl)benzonitrile (7m);
4-(1-[4-(4-[(11aS)-7-methoxy-5-oxo-2,3,5,11a-tetrahydro-1H-benzo[e]pyrrolo[1,2-a]azepin-8-yl]oxybutyl)piperazino]carbonylimidazo[1,5-a]pyridin-3-yl)benzonitrile (7n);
4-(1-[4-(5-[(11aS)-7-methoxy-5-oxo-2,3,5,11a-tetrahydro-1H-benzo[e]pyrrolo[1,2-a]azepin-8-yl]oxypentyl)piperazino]carbonylimidazo[1,5-a]pyridin-3-yl)benzonitrile (7o);
4-(1-[4-(6-[(11aS)-7-methoxy-5-oxo-2,3,5,11a-tetrahydro-1H-benzo[e]pyrrolo[1,2-a]azepin-8-yl]oxyhexyl)piperazino]carbonylimidazo[1,5-a]pyridin-3-yl)benzonitrile (7p);
(11aS)-8-[3-(4-[3-(4-fluorophenyl)imidazo[1,5-a]pyridin-1-yl]carbonylpiperazino) propoxy]-7-methoxy-2,3,5,11a-tetrahydro-1H-benzo[e]pyrrolo[1,2-a]azepin-5-one (7q);
(11aS)-8-[4-(4-[3-(4-fluorophenyl)imidazo[1,5-a]pyridin-1-yl]carbonylpiperazino)butoxy]-7-methoxy-2,3,5,11a-tetrahydro-1H-benzo[e]pyrrolo[1,2-a]azepin-5-one (7r);
(11aS)-8-[5-(4-[3-(4-fluorophenyl)imidazo[1,5-a]pyridin-1-yl]carbonylpiperazino) pentyl]oxy-7-methoxy-2,3,5,11a-tetrahydro-1H-benzo[e]pyrrolo[1,2-a]azepin-5-one (7s);
(11aS)-8-[6-(4-[3-(4-fluorophenyl)imidazo[1,5-a]pyridin-1-yl]carbonylpiperazino) hexyl]oxy-7-methoxy-2,3,5,11a-tetrahydro-1H-benzo[e]pyrrolo[1,2-a]azepin-5-one (7t);

(11aS)-8-[3-(4-[3-(4-chlorophenyl)imidazo[1,5-a]pyridin-1-yl]carbonylpiperazino) propoxy]-7-methoxy-2,3,5,11a-tetrahydro-1H-benzo[e]pyrrolo[1,2-a]azepin-5-one (7u);

(11aS)-8-[4-(4-[3-(4-chlorophenyl)imidazo[1,5-a]pyridin-1-yl]carbonylpiperazino) butoxy]-7-methoxy-2,3,5,11a-tetrahydro-1H-benzo[e]pyrrolo[1,2-a]azepin-5-one (7v);

(11aS)-8-[5-(4-[3-(4-chlorophenyl)imidazo[1,5-a]pyridin-1-yl]carbonylpiperazino) pentyl]oxy-7-methoxy-2,3,5,11a-tetrahydro-1H-benzo[e]pyrrolo[1,2-a]azepin-5-one (7w);

(11aS)-8-[6-(4-[3-(4-chlorophenyl)imidazo[1,5-a]pyridin-1-yl]carbonylpiperazino) hexyl]oxy-7-methoxy-2,3,5,11a-tetrahydro-1H-benzo[e]pyrrolo[1,2-a]azepin-5-one (7x).

3. The compound as claimed in claim 1, wherein the structural formula of the representative compounds 7(a-x) are:

(7a)

(7b)

(7c)

(7d)

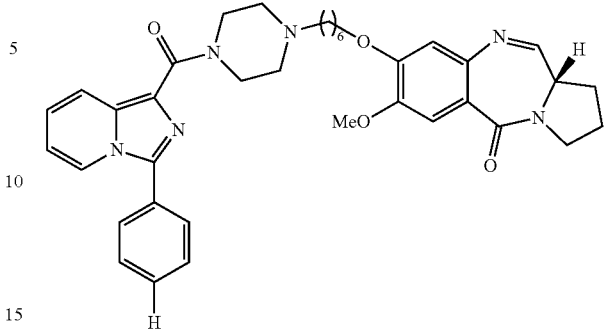

(7e)

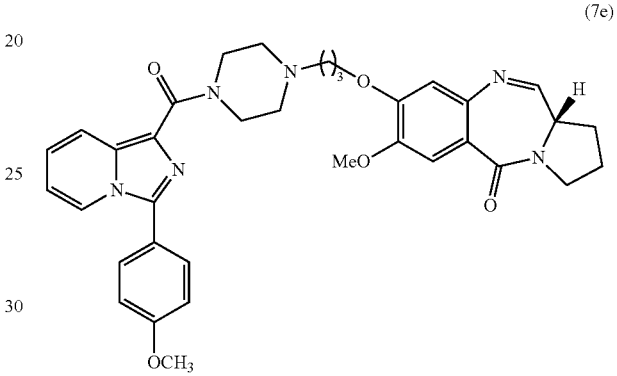

(7f)

(7g)

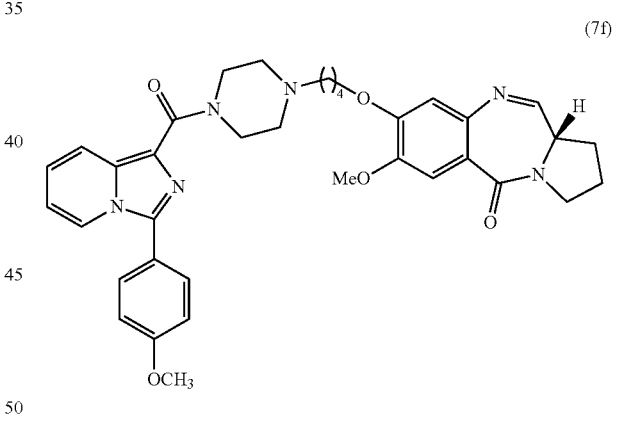

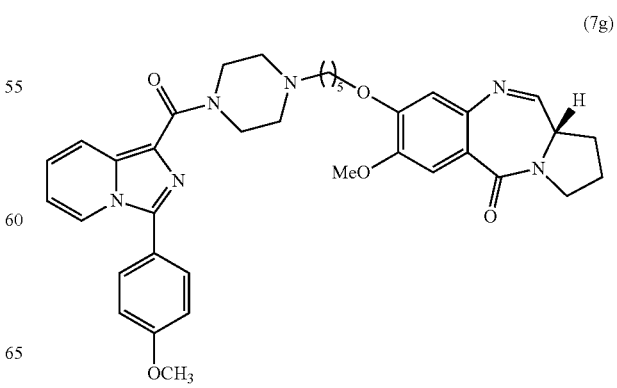

-continued
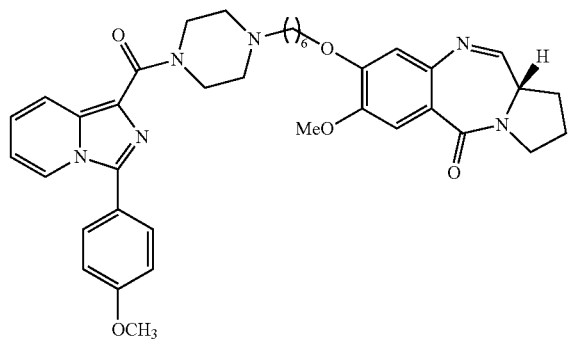
(7h)
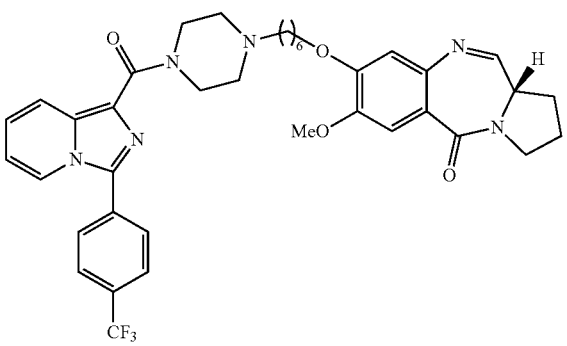
(7l)
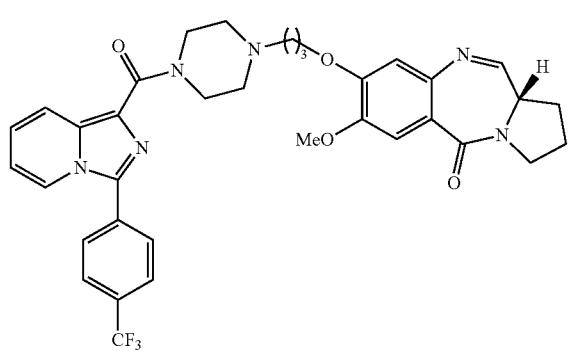
(7i)
(7m)
(7j)
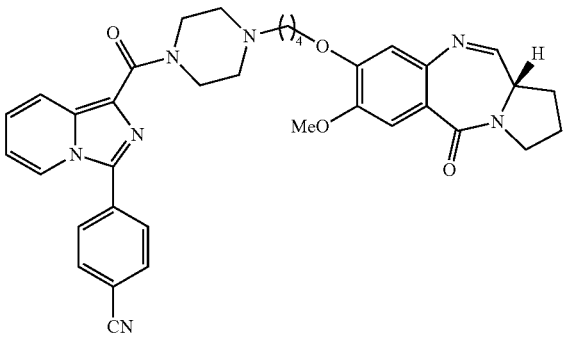
(7n)
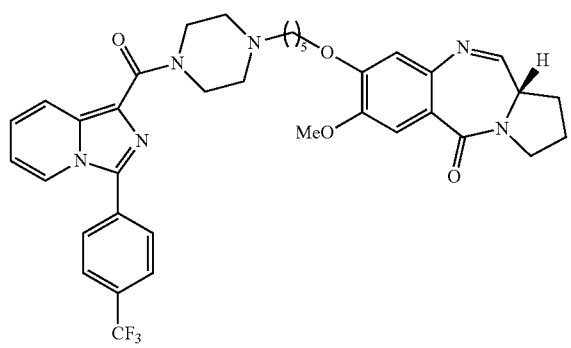
(7k)
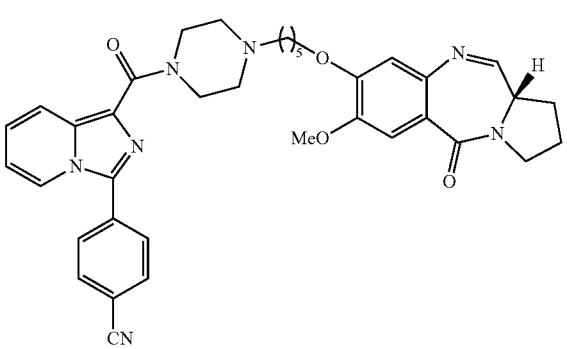
(7o)

(7p)
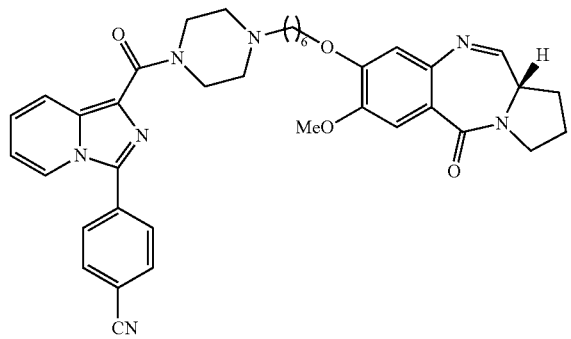
(7t)
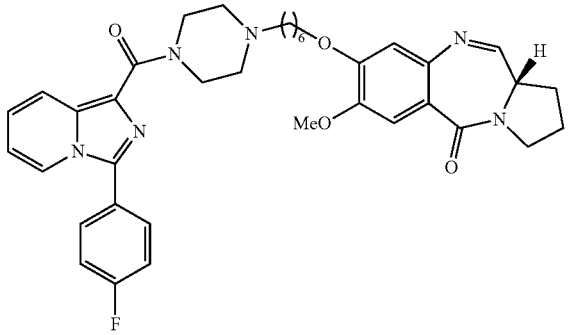
(7q)
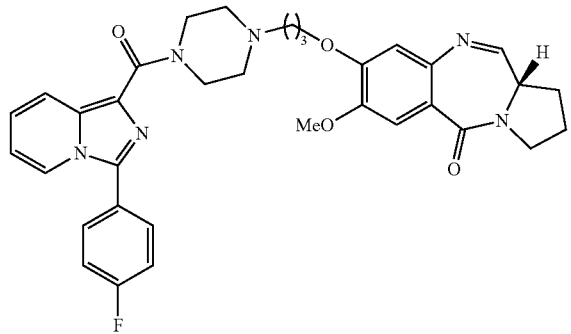
(7u)
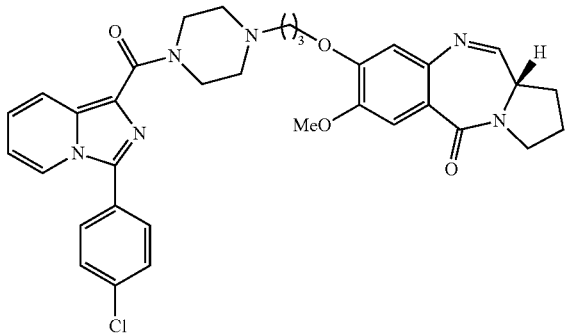
(7r)
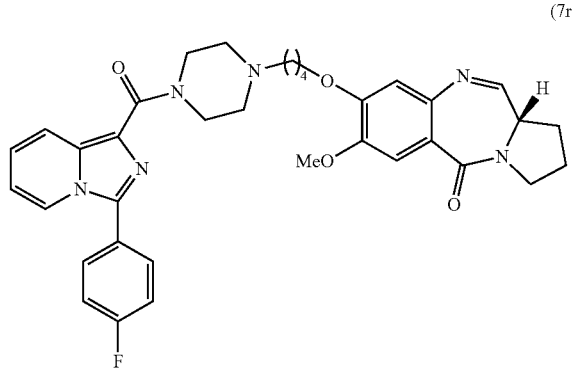
(7v)
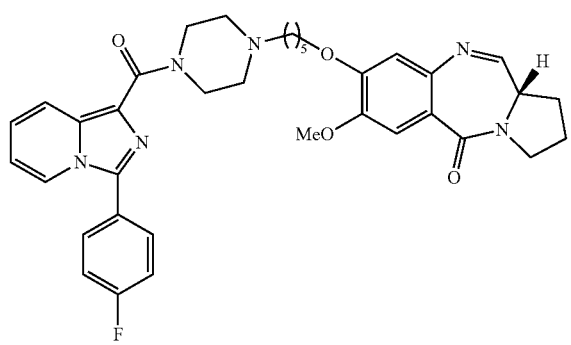
(7s)
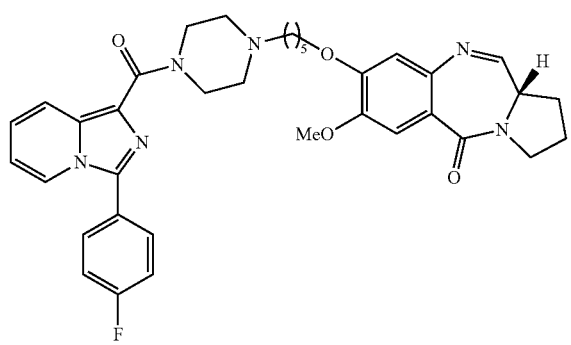
(7w)
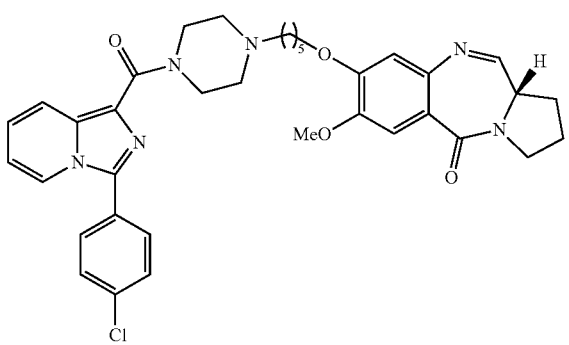

-continued

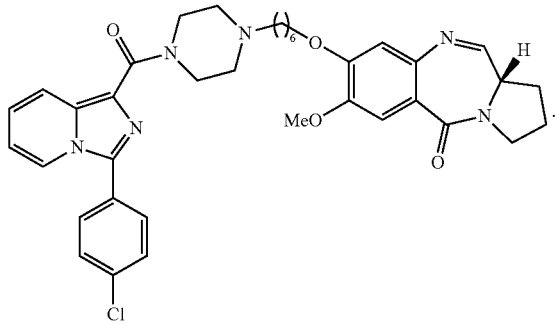

(7x)

4. A method of making the compound of claim 1 comprising:

a) reacting a compound of formula 2 with a compound of formula 4 in a 1:1 ratio in the presence of $K_2CO_3$ in acetone solvent at refluxing temperature in the range of 56 to 60° C. to obtain the resultant nitro compound of formula 5:

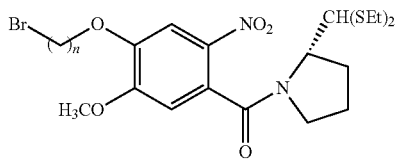

2

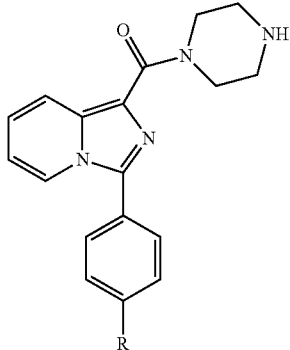

4

-continued

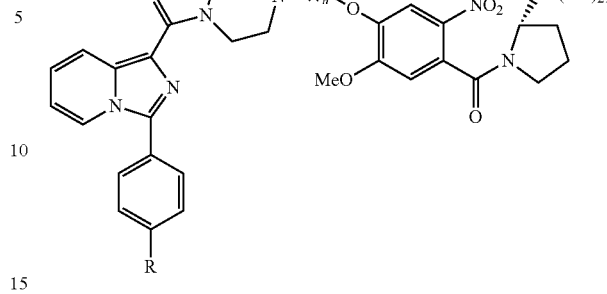

5 b) reducing the nitro compound of formula 5 as obtained in step (a) with $SnCl_2:2H_2O$ in a 1:3 ratio in methanol solvent at a temperature in the range of 66 to 70° C. to obtain an amino compound of formula 6:

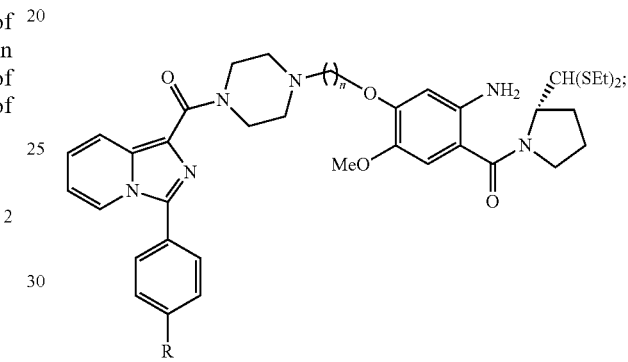

6 and c) reacting the amino compound of formula 6 as obtained in step (b) with a deprotecting agent $HgCl_2$ in acetonitrile-water in a 4:1 ratio to obtain the desired compound.

5. The compound of claim 2, wherein the compound is 7a.
6. The compound of claim 2, wherein the compound is 7b.
7. The compound of claim 2, wherein the compound is 7c.
8. The compound of claim 2, wherein the compound is 7d.
9. The compound of claim 2, wherein the compound is 7e.
10. The compound of claim 2, wherein the compound is 7f.
11. The compound of claim 2, wherein the compound is 7g.
12. The compound of claim 2, wherein the compound is 7h.
13. The compound of claim 2, wherein the compound is 7i.
14. The compound of claim 2, wherein the compound is 7j.
15. The compound of claim 2, wherein the compound is 7k.
16. The compound of claim 2, wherein the compound is 7l.

* * * * *